United States Patent
Pereira et al.

(10) Patent No.: US 6,838,419 B2
(45) Date of Patent: Jan. 4, 2005

(54) MIXTURES OF QUATERNARY COMPOUNDS

(75) Inventors: Abel G. Pereira, Belleville, NJ (US); Helena S. Barinova, Iselin, NJ (US)

(73) Assignee: Croda, Inc., Parsippany, NJ (US)

( * ) Notice: Subject to any disclaimer, the term of this patent is extended or adjusted under 35 U.S.C. 154(b) by 0 days.

(21) Appl. No.: 10/788,169

(22) Filed: Feb. 26, 2004

(65) Prior Publication Data

US 2004/0167057 A1 Aug. 26, 2004

Related U.S. Application Data

(63) Continuation of application No. 10/339,550, filed on Jan. 9, 2003.
(60) Provisional application No. 60/403,041, filed on Aug. 13, 2002, and provisional application No. 60/347,005, filed on Jan. 9, 2002.

(51) Int. Cl.[7] .............................. C11D 1/62; C11D 1/645
(52) U.S. Cl. .................. 510/123; 510/124; 510/119; 510/130; 510/287; 510/308; 510/329; 510/330; 510/504; 510/515
(58) Field of Search ................. 510/308, 329, 510/330, 504, 515, 287, 119, 123, 124, 130

(56) References Cited

U.S. PATENT DOCUMENTS

| | | |
|---|---|---|
| 1,985,424 A | 12/1934 | Piggott |
| 2,438,091 A | 3/1948 | Lynch |
| 2,528,378 A | 10/1950 | Mannheimer |
| 2,658,072 A | 11/1953 | Kosmin |
| 2,703,798 A | 3/1955 | Schwartz |
| 2,965,576 A | 12/1960 | Wilson |
| 3,155,591 A | 11/1964 | Hilfer |
| 3,755,560 A | 8/1973 | Dickert |
| 3,929,678 A | 12/1975 | Laughlin et al. |
| 3,959,461 A | 5/1976 | Bailey et al. |
| 4,102,795 A | 7/1978 | Minegishi et al. |
| 4,128,484 A | 12/1978 | Barford et al. |
| 4,149,551 A | 4/1979 | Benjamin et al. |
| 4,152,272 A | 5/1979 | Young |
| 4,185,017 A | 1/1980 | Piesch et al. |
| 4,187,289 A | 2/1980 | Eckhardt |
| 4,206,195 A | 6/1980 | Bolich et al. |
| 4,228,042 A | 10/1980 | Letton |
| 4,247,538 A | 1/1981 | Barker |
| 4,259,217 A | 3/1981 | Murphy |
| 4,275,055 A | 6/1981 | Nachtigal et al. |
| 4,387,090 A | 6/1983 | Bolich, Jr. |
| 4,411,884 A * | 10/1983 | Jacquet et al. ............. 424/47 |
| 4,417,995 A | 11/1983 | Lips et al. |
| 4,421,769 A | 12/1983 | Dixon et al. |
| 4,452,732 A | 6/1984 | Bolich, Jr. |
| 4,557,853 A | 12/1985 | Collins |
| 4,704,272 A | 11/1987 | Oh et al. |
| 4,741,855 A | 5/1988 | Grote et al. |
| 4,788,006 A | 11/1988 | Bolich, Jr. et al. |
| 4,851,141 A | 7/1989 | Demangeon et al. |
| 4,855,440 A | 8/1989 | Shumway et al. |
| 4,891,214 A | 1/1990 | Stevens et al. |
| 4,902,499 A | 2/1990 | Bolich, Jr. et al. |
| 4,919,934 A | 4/1990 | Deckner et al. |
| 4,948,520 A | 8/1990 | Sasaki |
| 4,954,335 A | 9/1990 | Janchipraponevj |
| 4,976,953 A | 12/1990 | Orr et al. |
| 5,011,681 A | 4/1991 | Ciotti et al. |
| 5,120,532 A | 6/1992 | Wells et al. |
| 5,126,061 A * | 6/1992 | Michael .................. 252/86 |
| 5,151,209 A | 9/1992 | McCall et al. |
| 5,151,210 A | 9/1992 | Steuri et al. |
| 5,382,377 A | 1/1995 | Raehse et al. |
| 5,455,025 A | 10/1995 | Pereira et al. |
| 5,597,555 A | 1/1997 | Pereira et al. |
| 5,804,219 A | 9/1998 | Trinh et al. |

FOREIGN PATENT DOCUMENTS

| | | |
|---|---|---|
| EP | 095238 A2 | 11/1983 |
| JP | 58-144174 A1 | 8/1983 |
| JP | 60-81376 A1 | 5/1985 |

OTHER PUBLICATIONS

U.S. patent application Ser. No. 10/339,551, Pereira.
Fisher, J.P. and Lohr, K., Organic Coatings Science Technology, vol. 8, pp. 227–249, Marcel Dekker, Inc., Apr. 1986.
Segarin et al., Cosmetics Science and Technology, Chapter VIII, pp. 189 et seq.

* cited by examiner

Primary Examiner—Charles Boyer
(74) Attorney, Agent, or Firm—Lerner, David, Littenberg, Krumholz & Mentlik, LLP

(57) ABSTRACT

Compositions that include mixtures of (a) at least one dialkyl quat in the amount of from about 10% to about 90% by weight of the composition; and (b) at least one monoalkyl quat in the amount of from about 10% to about 90% by weight of the composition are provided. Various embodiments are provided. In one embodiment, the mixtures include dialkyl immidazoline quats and monoalkyl immidazoline quats. In one embodiment, the mixtures include dialkyl immidazoline quats and monoalkyl ammonium quats. Various methods of making immidazoline quats and quat mixtures, personal care and cosmetic products and formulations that contain the immidazoline quats and quat mixtures, methods of making such personal care and cosmetic products and formulations, and methods of using the such immidazoline quats, quat mixtures, and personal care and cosmetic products and formulations are also provided.

44 Claims, No Drawings

MIXTURES OF QUATERNARY COMPOUNDS

CROSS REFERENCE TO RELATED APPLICATIONS

This patent application is a continuation of U.S. patent application Ser. No. 10/339,550, filed Jan. 9, 2003, which application claims the benefit of the filing date of U.S. Provisional Application No. 60/347,005, filed Jan. 9, 2002, and the benefit of the filing date of the U.S. Provisional Application No. 60/403,041, filed Aug. 13, 2002, the disclosures of both of which are hereby incorporated by reference in their entirety.

FIELD OF THE INVENTION

The present invention relates to the field of chemical manufacture and in particular, personal care products and cosmetics. It provides compositions that include quaternary compounds various personal care and cosmetic products, formulations that include such compositions, as well as methods of their manufacture, use, and other related methods.

BACKGROUND OF THE INVENTION

EMULSIONS AND EMULSIFICATION

An emulsion, more precisely a liquid/liquid emulsion, is a two-phase system of two immiscible liquids (usually, incompletely immiscible), with one of the phases being dispersed in the form of droplets in the other phase. Emulsions are preferred forms for the cosmetic and personal care products because they allow for the combination of otherwise immiscible ingredients and can provide significant economic advantages. Also, the public favors the feel and look of the emulsions. For these reasons, among others, a large proportion of modern cosmetic and personal care products are emulsions, and the process of producing emulsions (or emulsification) is a very important process in the cosmetic and personal care industries.

As described, emulsions' two liquid phases do not form a single phase upon mixing. It is believed that the primary reason for this immiscibility is the difference in the polarity of the molecules that comprise each liquid phase. Usually, one phase is relatively lipophilic or non-polar, while the other is relatively hydrophilic or polar.

If the phases (e.g., water and oil) are combined without any agitation, they usually (although not necessarily) form two separate layers with a single phase-separation boundary between the layers. Emulsification typically involves agitation to disperse one phase throughout the other. Such dispersion leads to an increase in the area of surface contact between the phases, which have drastically different polarities. It is believed that the increase in the area of surface contact increases surface tension or surface energy of the phases.

For this reason, most emulsions are thought to be thermodynamically unfavorable and therefore inherently unstable after formation. To minimize the area of surface contact and the surface energy when left alone over time, emulsions tend to separate back into two layers with a single phase-separation boundary.

Since the products formulated as emulsions are usually stored for substantial periods of time prior to use, this separation of phases is highly undesirable. To prevent phase separation, formulators usually add various emulsifiers. The emulsifiers are surface-active compounds or surfactants that are believed to reduce the surface tension of the phases, thus reducing the thermodynamic drive for phase separation and improving the stability of emulsions.

The emulsifiers are usually compounds having both hydrophilic and lipophilic groups in the molecule. Somewhat oversimplifying, the hydrophilic groups contact the hydrophilic phase of the emulsion, and the lipophilic groups contact the lipophilic phase, in effect tying the phases together and acting to prevent phase separation. The selection and utilization of emulsifiers is one of the challenges in formulating emulsions.

QUATERNARY COMPOUNDS

Personal care and cosmetic products often contain various surfactants, including cationic surfactants having a quaternary nitrogen atom (or quats). Quats are commonly used in hair care products. It is known that hair may be negatively affected by atmospheric agents, chemical treatments, and the like, resulting in damaged hair, which lacks softness and which may be difficult to disentangle or style. Quats facilitate disentangling and combing of hair, and provide softness to the hair, and thus they are used as active ingredients of hair care products, such as hair conditioners and conditioning shampoos.

Various types of quats are known in the art. Ammonium quats that contain quaternized ammonium nitrogen

are described, for example, in U.S. Pat. Nos. 4,954,335 and 4,891,214. Examples of such quats include dibehenyl dimethyl ammonium quat sold under the trade name INCROQUAT DBM-90 from Croda Incorporated, 7 Century Drive, Parsippany, N.J. 07054. Other examples of ammonium quats used in hair care products are cetyltrimethylammonium bromide and behenyltrimethylammonium bromide.

Other types of quats are also known in the art. Imidazoline-based quats containing the imidazoline ring

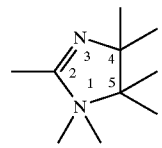

are disclosed, for example, in U.S. Pat. Nos. 4,851,141, 4,452,732, 4,247,538, 4,206,195, 4,187,289, 4,149,551, and 4,102,795.

U.S. Pat. No. 4,102,795 discloses compositions for softening fabrics or hair that include imidazoline-based quarternary compounds of the formula

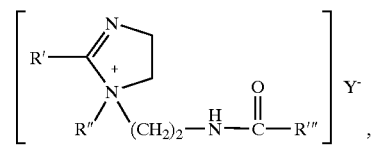

where R' and R''' are alkyl groups having 11 to 22 carbon atoms, or β-hydroxyalkyl groups having from 13 to 24 carbon atoms; R'' is an alkyl group having 1 to 3 carbon atoms, benzyl group, or the group —$(C_2H_4O)_nH$, where n is 1 to 3; and $Y^-$ is halogen or monoalkyl sulfate. The '795 patent mentions the possibility of mixtures of these imidazoline-based compounds, but does not provide their content or other information about such mixtures.

U.S. Pat. No. 4,452,732 discloses a shampoo containing several components, including imidazoline-based quaternary compounds of the formula

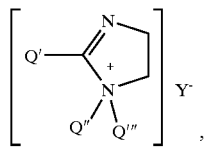

where at least one of, and preferably both of the groups Q' and Q''' is/are a hydrocarbon group(s) containing 16 to 22 carbon atoms, preferably, 16 to 18 carbon atoms; Q'' is $C_1$–$C_4$ alkyl or hydroxyalkyl group; and $Y^-$ is a compatible anion. Mixtures are mentioned, but again, the mention is without information about their content, and no specific mixtures are disclosed.

Primarily, the imidazoline-based quats and the ammonium quats are disclosed as pure compounds. While mixtures of quats or mixtures with different surfactants had been mentioned in general, the prior art provides no specific mixtures or other information about the mixtures. Also, the prior art does not provide information about the relationships between primary product performance, such as performance in hair conditioning products, and emulsification characteristics of quats and/or quat mixtures in emulsion-formulated products.

SUMMARY OF THE INVENTION

The present invention relates to compositions that include certain mixtures of quats. The aspects of the invention include such mixtures of quats, methods of making such quat mixtures, personal care and cosmetic products and formulations that contain these quat mixtures, methods of making such personal care and cosmetic products and formulations, and methods of using the such quat mixtures, products and formulations.

In one aspect, the invention provides compositions that include mixtures of (a) at least one dialkyl quat in the amount of from about 10% to about 90% by weight of the composition; and (b) at least one monoalkyl quat in the amount of from about 10% to about 90% by weight of the composition.

Various embodiments are provided. In one embodiment, the mixtures include dialkyl imidazoline quats and monoalkyl imidazoline quats. In one embodiment, the mixtures include dialkyl imidazoline quats and monoalkyl ammonium quats.

Also provided is a method of improving formulation of hair conditioning products by providing mixtures of (a) at least one dialkyl quat in the amount of from about 10% to about 90% by weight of the composition; and (b) at least one monoalkyl quat in the amount of from about 10% to about 90% by weight of the composition. The mixture of two components, wherein one component is selected for primary product performance, and another component is selected for its contribution to proper emulsification of the hair conditioning product but essentially does not detract from the primary product performance. Methods of making imidazoline quats and quat mixtures, personal care and cosmetic products and formulations that contain the imidazoline quats and quat mixtures, methods of making such personal care and cosmetic products and formulations, and methods of using the such imidazoline quats, quat mixtures, and personal care and cosmetic products and formulations are also provided. Various embodiments of the methods are disclosed.

DESCRIPTION OF THE PREFERRED EMBODIMENTS

For the purposes of the present invention, various terms used herein are defined as follows. A "compound" is a distinct chemical substance having molecules of the same chemical structure. A "compound" is not a mixture of molecules having different chemical structures. A "composition" may include one compound or a mixture of compounds.

An "alkyl group" is any substituent group that includes a chain of one or more carbon atoms. An alkyl group may terminate in alkyl functionality (e.g., —$CH_3$) or non-alkyl functionality (e.g., —Br). Likewise, an alkyl group may connect to the rest of the molecule (MOL) through alkyl functionality (e.g., —$CH_2$— in MOL-$CH_2CH_3$) or non-alkyl functionality (e.g., —$SO_2$— in MOL-$SO_2C_3H_8$). Purely for purposes of illustration, each of the groups —$(CH_2)_3$—OH, —$(CH_2)_4$—$CH_3$, —$CH_3$, and —C(O)—$(CH_2)_5$—$CH_3$, is an alkyl group. An "alkyl radical" is a chain of one or more carbon atoms connected to one another. Purely for purposes of illustration, the alkyl groups —$(CH_2)_3$—OH, —$(CH_2)_4$—$CH_3$, and —C(O)—$(CH_2)_5$—$CH_3$ contain alkyl radicals of the structures —$(CH_2)_3$—, —$(CH_2)_4$—$CH_3$, and —$(CH_2)_5$—$CH_3$, respectively.

Carbon chains of alkyl groups and alkyl radicals, and alkyl groups and radicals themselves are described as "$C_x$–$C_y$." An alkyl group containing a $C_x$–$C_y$ alkyl radical is referred to as $C_x$–$C_y$ alkyl. Such description encompasses carbon chains of every length ranging from x to y carbon atoms, inclusive. For example, the description of an alkyl radical as "$C_{10}$–$C_{20}$" encompasses all alternative carbon chains having from 10 to 20 carbon atoms, including carbon chains having 10, 11, 12, 13, 14, 15, 16, 17, 18, 19, and 20 carbon atoms.

Terms such as alkylhydroxy, alkylcarboxy, carboxyalkyl, and the like, are used throughout. Purely for purposes of illustration, an alkylhydroxy group contains a hydroxy group and an alkyl radical, and connects to the rest of the molecule through the alkyl radical; a carboxyalkyl group contains an alkyl radical and a carboxy functionality that connects the carboxy group to the rest of the molecule; an alkylcarboxy group connects to the rest of the molecule through an alkyl radical and terminates in a carboxy functionality. Purely for purposes of illustration, "$C_{10}$–$C_{30}$ alkyl" defines a range of alkyl groups containing alkyl radicals having from 10 to 30 carbon atoms and "$C_{10}$–$C_{30}$ alkylhydroxy" defines a range of alkyl groups containing a hydroxy group and alkyl radicals having from 10 to 30 carbon atoms.

In the compounds described herein, and consistent with the definitions set forth above, the alkyl groups and alkyl radicals, when present, may be substituted or unsubstituted, straight chain or branched, saturated or unsaturated. The substituents of the alkyl groups and alkyl radicals described herein, when present, may include lower alkyl, which contain alkyl radicals having from 1 to 8 carbon atoms (e.g., methyl, ethyl, n-propyl, i-propyl, and butyl); halogenated lower alkyl, such as trifluoromethyl, perfluoroethyl, chloromethyl, and dichloromethyl; arylalkyl, such as benzyl; alkylaryl, such as p-methylbenzyl; halo, such as fluoro, chloro and bromo; carboxy, such as acetoxy and ethylcarboxy; alkylcarboxy, such as acetoxymethyl and acetoxyethyl; arylacetoxy, such as acetylbenzyl; hydroxy; alkoxy, such as methoxy, ethoxy and propoxy; and alkylhydroxy, such as hydroxymethyl and hydroxyethyl.

Dialkyl quats are compounds the molecules of which include a quaternary nitrogen atom and two alkyl groups or alkyl radicals having 10 or more carbon atoms. Dialkyl imidazoline quats are compounds the molecules of which include an imidazoline ring, a quaternary nitrogen atom, and two alkyl groups having 10 or more carbon atoms (two $C_{10+}$ alkyl groups). Dialkyl ammonium quats are compounds the molecules of which include a quaternary ammonium nitrogen atom and two alkyl groups or alkyl radicals having 10 or more carbon atoms.

Monoalkyl quats are compounds the molecules of which include a quaternary nitrogen atom and one alkyl group or alkyl radical having 10 or more carbon atoms. Monoalkyl imidazoline quats are compounds the molecules of which include an imidazoline ring, a quaternary nitrogen atom, and one alkyl group having 10 or more carbon atoms (one $C_{10+}$ alkyl group). Monoalkyl ammonium quats are compounds the molecules of which include a quaternary ammonium nitrogen atom and one alkyl group or alkyl radical having 10 or more carbon atoms.

Mixtures of quat compounds are described herein in terms of their substitution content, which is a characteristic of the quat mixture as a whole. The substitution content of a quat mixture is a ratio, expressed in the percentage terms, of the molar content of the alkyl groups that fall within a specified substitution range to the molar content of the alkyl groups that fall within a broader, reference substitution range. The molar content values for both the specified substitution range and the reference substitution range are measured for the quat mixture as a whole.

The specified substitution ranges are denoted as "$C_{x-y}$", indicating a range alkyl groups or alkyl radicals having from x to y carbon atoms. The reference substitution ranges are denoted as "$C_{X-Y}$" or "$C_{10+}$". "$C_{10+}$" indicates a range of alkyl group or alkyl radicals having 10 or more carbon atoms. "$C_{X-Y}$" indicates a range of alkyl groups or alkyl radicals having from X to Y carbon atoms.

The quat mixtures are described in terms of their "$C_{x-y}$ content" or "$C_{x-y}$ substitution content". The $C_{10+}$ reference range is the default substitution range. Thus, unless specified otherwise, a $C_{x-y}$ substitution content of a quat mixture (abbreviated in the exemplified mixtures throughout as "$S_{x-y}$") is the ratio, expressed in the percentage terms, of the molar content of alkyl groups that fall within a $C_{x-y}$ range ("$M_{x-y}$") to the molar content of the alkyl groups that fall within the $C_{10+}$ range ("$M_{10+}$"): $S_{x-y}=M_{x-y}/M_{10+}\times 100\%$, where both $M_{x-y}$ and $M_{10+}$ are measured for the mixture as a whole. If any reference range other than $C_{10+}$ is used to describe a quat mixture (e.g., $C_{x-y}$ range), the substitution content of the mixture (abbreviated in the exemplified mixtures as "$S_{x-y/X-Y}$") and is the ratio of the molar content of alkyl groups that fall within a specified $C_{x-y}$ range ("$M_{x-y}$") to the molar content of the alkyl groups that fall within the $C_{X-Y}$ reference range ("$M_{X-Y}$"): $S_{x-y/X-Y}=M_{x-y}/M_{X-Y}\times 100\%$.

To illustrate, consider the mixture M1 that contains a single molecule of dialkyl quat A1 and a single molecule of different dialkyl imidazoline quat A2. By definition, each of dialkyl quats $A_1$ and A2 has two $C_{10+}$ alkyl groups. Suppose, the molecule of quat A1 has one $C_{20}$ alkyl group and one $C_{12}$ alkyl group, and the molecule of quat A2 has two $C_{20}$ alkyl groups. Suppose also, the mixture M1 is to be characterized in terms of its $C_{16-30}$ substitution content ($S_{16-30}$(M1)), e.g., the narrower, specified range is $C_{16-30}$ and the broader, reference range is $C_{10+}$.

The $C_{16-30}$ substitution content of the mixture M1 can be calculated as: $S_{16-30}(M1)=M_{16-30}(M1)/M_{10+}(M1)\times 100\%$, where $M_{16-30}$ is the $C_{16-30}$ molar content of the mixture M1 and $M_{10+}(M1)$ is the $C_{10+}$ molar content of the mixture M1. Since the molar concentrations of quats A1 and A2 in the mixture M1 are identical (one molecule each), the relative molar concentration may be disregarded, and the absolute numbers of alkyl groups falling within each range may be used instead. Thus, the $C_{16-30}$ substitution content of the mixture M1 as a whole may be calculated as: $S_{16-30}(M1)=N_{16-30}(M1)/N_{10+}(M1)\times 100\%$, where $N_{16-30}(M1)$ is the number of alkyl groups in the mixture M1 that fall within the $C_{16-30}$ range and $N_{10+}(M1)$ is the number of alkyl groups in the mixture M1 falling within the $C_{10+}$ range.

The first step is to calculate the values of $N_{16-30}$ and $N_{10+}$ for the mixture. To determine $N_{16-30}$ and $N_{10+}$, a substituent group is counted every time it falls within the $C_{10+}$ and $C_{16-30}$ ranges, respectively, for all molecules in the mixture. The same group may be counted more than once. The $C_{20}$ group falls within both the $C_{16-30}$ range and the $C_{10+}$ range and thus should be counted in calculating both $N_{16-30}(M1)$ and $N_{10+}(M1)$, while the $C_{12}$ group fall only within the $C_{10+}$ range and therefore should be counted only in calculating $N_{10+}(M1)$. Performing the calculation for the mixture M1 as a whole, $N_{16-30}$ is 3 (one $C_{20}$ group of quat A1 and two $C_{20}$ group of the quat A2) and $N_{10+}$ is 4 (all four groups are in the $C_{10+}$ range). Therefore, $S_{16-30}$ for the mixture M1 is 75% (3/4×100%).

For more complex quat mixtures, molar concentrations of quats in the mixture are taken into account. A non-limiting example illustrates calculation of substitution content for mixture M2 of dialkyl quats A3, A4, and A5. The mixture M2 is characterized in terms of its $C_{20-30}$ substitution content (the specified substitution range is $C_{20-30}$ and the reference substitution range is $C_{10+}$):

TABLE 1*

| I | II<br>($N_{20-30}$) | III<br>($P_{20-30}$) | IV<br>($M_0//M_{10+}$) | V<br>($M_{20-30}$) | VI<br>($S_{20-30}$) |
|---|---|---|---|---|---|
| Quat | Number of alkyl groups in the quat molecule falling in the $C_{20-30}$ range | $C_{20-30}$ molecular content for each quat ((II)/2) | Moles | $C_{20-30}$ molar contribution of each quat ((III) × ((IV)) and $C_{20-30}$ molar content of the mixture | $C_{20-30}$ substitution content of the mixture |
| A3 | 1 (one) | 0.5 | 2 | 1 (0.5 × 2) | |
| A4 | 2 (two) | 1 | 0.75 | 0.75 (1 × 0.75) | |

TABLE 1*-continued

| I | II ($N_{20-30}$) | III ($P_{20-30}$) | IV ($M_0$//$M_{10+}$) | V ($M_{20-30}$) | VI ($S_{20-30}$) |
|---|---|---|---|---|---|
| A5 | 0 (none) | 0 | 0.75 | 0 (0 × 0.75) | |
| M2 | | | 3.5 | 1.75 | 50% (1.75/3.5) |

*Column (I) identifies quat components of the mixture M2. Column (II) indicates how many alkyl groups of each quat molecule fall within the $C_{20-30}$ range (note that dialkyl quats have two groups in the $C_{10+}$ range ($N_{10+}$ is 2)). Column (IV) provides molar amounts of each quat in the mixture M2 and the total number of quat moles in the mixture M2. Columns (III), (V) and (VI) are explained below.

To calculate the $C_{20-30}$ substitution content ($S_{20-30}$) of the mixture M2, the first step is to determine the $C_{20-30}$ content the molecule of each quat based on its chemical structure. Such substitution content is referred to as $C_{20-30}$ "molecular content" and denoted as "$P_{20-30}$". The $C_{20-30}$ molecular content of a quat is determined by dividing the number of $C_{20}$–$C_{30}$ alkyl groups ($N_{20-30}$) by the number of $C_{10+}$ alkyl groups ($N_{10+}$) in molecule of the quat: $P_{20-30}=N_{20-30}/N_{10+}$.

In the example, the nature of substitution for quats in the mixture is provided in column (II). The molecule of quat A3 has 1 (one) group that falls in the $C_{20-30}$ range. The number of groups in the $C_{10+}$ range is 2 (two) for all dialkyl quats. Thus, the $C_{20-30}$ molecular content of quat A3 ($P_{20-30}$ (A3)) is 1/2=0.5. The $C_{20-30}$ molecular content values for quats A3, A4, and A5 are calculated in the same manner by dividing the values in column (II) by 2, and are shown in column (III).

Next, the $C_{20-30}$ molar contribution of each quat component of the mixture ($M_{20-30}$) is calculated. For this purpose, each quat's $C_{20-30}$ molecular content ($P_{20-30}$, column (III)) is multiplied by the number of moles of the corresponding quat in the mixture ($M_0$, column (IV)): $M_{20-30}=P_{20-30}\times M_0$. The results of the calculations are shown in column (V). In effect, the product of the multiplication is the molar amount of $C_{20-30}$ alkyl groups contributed by each quat component of the mixture M2.

The $C_{20-30}$ molar content of the mixture M2 as a whole ($M_{20-30}$(M2)) is the sum of the $C_{20-30}$ molar contributions of individual quats: $M_{20-30}$(M2)=$M_{20-30}$(A3)+$M_{20-30}$(A4)+$M_{20-30}$(A5). Referring to column (V), quat A3 contributes 1 mole of $C_{20}$–$C_{30}$ groups ($M_{20-30}$(A3)=1), quat A4 contributes 0.75 moles ($M_{20-30}$(A4)=0.75), and quat A5 contributes 0 moles of $C_{20}$–$C_{30}$ groups ($M_{20-30}$(A5)=0). Therefore, the $C_{20-30}$ molar content of the mixture M2 is 1.75 ($M_{20-30}$(M2)=1+0.75+0).

The sum of the $C_{10+}$ molar contributions of individual quats is the $C_{10+}$ molar content of the mixture M2 as a whole ($M_{10+}$(M2)=$M_{10+}$(M2)=$M_{10+}$(A3)+$M_{10+}$(A4)+$M_{10+}$(A5). Since all dialkyl quats have two alkyl groups in the $C_{10+}$ range, the $C_{10+}$ molar content ($M_{10+}$) of a dialkyl quat component is identical to the number of moles of the quat component ($M_0$). Referring to column (IV), quat A3 contributes 2 mole of $C_{10+}$ groups ($M_{0+}$(A3)=2), quat A4 contributes 0.75 moles ($M_{0+}$(A4)=0.75), and quat A5 contributes 0.75 moles of $C_{10+}$ groups ($M_{0+}$(A5)=0.75). Therefore, the $C_{10+}$ molar content of the mixture M2 is 3.5 ($M_{10+}$(M2)=2+0.75+0.75). Finally, the $C_{20-30}$ substitution content of the mixture M2 can be calculated: $S_{20-30}$(M2)= $M_{20-30}$(M2)/$M_{10+}$(M2)=1.75/3.5=50% (column (VI)).

Another non-limiting example illustrates calculation of the substitution content for mixtures of monoalkyl quats. Table 2 shows mixture M3 of monoalkyl quats B1, B2, and B3. The mixture M3 is characterized in terms of its $C_{20-24}$ substitution content (the specified substitution range is $C_{20-24}$ and the reference substitution range is $C_{10+}$).

TABLE 2

| I | II ($N_{20-24}$) | III ($P_{20-24}$) | IV ($M_0$//$M_{10+}$) | V ($M_{20-24}$) | VI ($S_{20-24}$) |
|---|---|---|---|---|---|
| Quat | Number of alkyl groups (the $C_{20-24}$ range) that fall in the quat molecule | $C_{20-24}$ molecular content for each quat (II/1) | Moles | $C_{20-24}$ molar contribution of each quat (III × IV) and $C_{20-24}$ molar content the mixture | $C_{20-24}$ substitution content of the mixture (V/IV) |
| B1 | 1 | 1 | 1.5 | 1.5 (1 × 1.5) | |
| B2 | 1 | 1 | 1 | 1 (1 × 1) | |
| B3 | 0 | 0 | 2.5 | 0 (0 × 2.5) | |
| M3 | | | 5 | 2.5 | 2.5/5 × 100% = 50% |

The $C_{20-24}$ substitution content of the mixture M3 ($S_{20-24}$(M3)) is calculated as follows similarly to the calculations described in reference to the mixture of Table 1:

1. Determine the $C_{20-24}$ molecular content for each monoalkyl quat: $P_{20-24}=N_{20-24}/N_{10+}$. Since $N_{10+}$ is 1 (one) for all monoalkyl quats, the $C_{20-24}$ molecular content for each quat is calculated as: $P_{20-24}=N_{20-24}/1$. The results are shown in column (III). It is evident that $P_{x-y}=N_{x-y}$ for monoalkyl quats in general. Thus, $N_{x-y}$ may be used instead of $P_{x-y}$ and column (III) is omitted in later examples of monoalkyl quat mixtures.

2. Determine the $C_{20-24}$ molar contributions of quat components by multiplying the number of $C_{20}$–$C_{24}$ groups by molar amount for each quat component: $M_{20-24}=N_{20-24}\times M_0$. The $N_{20-24}$ values in column (II) are multiplied by the corresponding $M_0$ values in column (IV). The results of the calculations are in column (V).

3. Determine the $C_{20-24}$ molar content of the mixture M3 by adding the $C_{20-24}$ molar contributions of the quat components: $M_{20-24}(M3)=M_{20-24}(B1)+M_{20-24}(B2)+M_{20-24}(B3)$. The $M_{20-24}$ values for each quat component in column (V) are added. The calculated $C_{20-24}$ molar content of the mixture M3 is also shown in column (V).

4. Determine the $C_{10+}$ molar content of the mixture M3 by adding the $C_{10+}$ molar contributions of the quat components. Since all monoalkyl quats have one alkyl group in the $C_{10+}$ range, molar amounts of the quats are used: $M_{10+}(M3)=M_0(B1)+M_0(B2)+M_0(B3)$. The $M_0$ values for each quat component in column (IV) are added. The calculated $C_{10+}$ molar content of the mixture M3 is shown in column (IV).

5. Determine the $C_{20-24}$ substitution content of the mixture M3 by dividing the $C_{20-24}$ molar content of the mixture M3 by the $C_{10+}$ molar content of the quats in the mixture: $S_{20-24}(M3)=M_{20-24}(M3)/M_{10+}(M3)$. The calculated $C_{20-24}$ substitution content of the mixture M3 is shown in column (VI).

The above definitions and calculation methodologies are used throughout to describe various aspects and embodiments of the invention.

As described above, quats are useful as active ingredients in hair conditioning products. Their use in such products is related to primary purpose of product formulation (e.g., conditioning hair). Such primary purpose(s) of a product and the effectiveness of quats in effecting this purpose are referred to herein as "primary product performance." For example, in hair conditioning products, primary product performance of quats is related to their effectiveness in disentangling and/or softening hair, etc. Likewise, in shampoos, primary product performance is related to cleansing effectiveness.

The primary product performance of quats may be, and often is, unrelated to their effectiveness in forming and/or stabilizing emulations. It is believed that for many cosmetic and personal care products, the goals of primary product performance and emulsion formation, stability, and appearance are not entirely compatible. For example, conditioning or cleansing performance of a hair care product often depends on the nature and the concentration of quat(s) included in the product. However, the nature and concentrations of quats selected on the basis of their primary product performance may not be optimal, or even acceptable, for obtaining and/or stabilizing an emulsion.

For example, it has been discovered that dialkyl quats having longer-chain (e.g., $C_{20+}$) alkyl groups have improved performance in a number of personal care applications, such as hair conditioning products. At the same time, the presence of such quats with longer-chain alkyl groups tend to make emulsification more difficult and/or may adversely affect the stability of the emulsion. Without being limited to any specific theory, it is thought that an increase in the length of alkyl chains of a quat leads to an increase in the lipophilic character of the quat. As the length of the alkyl chain grows, the balance between lipophilisity and hydrophilicity of the quat molecule may shift so significantly that formulating emulsions may become difficult.

Even with shorter-chain dialkyl quats, for example, $C_{14}$–$C_{16}$ dialkyl quats, emulsification often requires presence of a separate emulsifier. However, the traditionally used, non-quat emulsifiers rarely contribute to the primary product performance, and each added ingredient complicates product formulation.

The following non-limiting example is helpful. A prior art hair conditioning composition could, for example, include 30% of dialkyl imidazoline quat of the formula (1), where R' and R''' are —$C_{15}H_{29}$. This compound may act both as an emulsifier and an active hair-conditioning ingredient. If $C_{15}H_{29}$ groups are replaced with $C_{22}H_{43}$, the hair conditioning performance of the composition may improve, but the addition of a non-quat emulsifying compound(s) may be necessary. However, as described above, such non-quat emulsifiers rarely contribute to hair conditioning performance. Nevertheless, to accommodate the addition of the emulsifier, the quat content may have to be reduced from the amount desired, further affecting the primary product performance that was the reason for chain length increase in the first place. For this reason, the chain length of dialkyl quats was typically kept in the $C_{14}$–$C_{18}$ range.

However, it has now been surprisingly discovered that monoalkyl quats may be used instead of non-quat emulsifiers in combination with dialkyl quats, allowing the use of dialkyl quats with longer alkyl chains. The monoalkyl quats both contribute to primary product performance (or at least don't detract from same) and emulsification at the same time, facilitating the balance between performance and emulsification.

Thus, in one embodiment, the present invention provides a composition that includes at least two components, wherein the first component is selected for primary product performance, and the second component is selected for its contribution to proper emulsification of the product, but wherein the second component essentially does not detract from primary product performance. Preferably, the first component is selected in such a manner that its use in a product would require addition of external emulsifiers or use of other emulsification techniques, methods, or substances to allow the use of the first component in formulating the product as an emulsion. Also, the primary product performance of the first component is preferably superior to the primary product performance of the second component.

In the preferred embodiment, the first component includes one or more dialkyl quats, and the second component includes one or more monoalkyl quats. In accordance with a preferred aspect and this embodiment, the invention provides compositions that include at least:

(a) one or more dialkyl quats in the amount of from about 10% to about 90% by weight; and (b) one or more monoalkyl quats in the amount of from about 90% to about 10% by weight; where the percentages are with respect to the sum of the weights of the components (a) and (b).

Preferably, the component (a) is included in the amount of from about 20% to about 80%, more preferably, from about 40% to about 70% by weight, and the component (b) in the amount of from about 80% to about 20%, more preferably, from about 30% to about 60% by weight.

Below, various dialkyl and monoalkyl quats and their mixtures are described in greater details. It should be understood that any combination of components (a) and (b) are contemplated.

COMPONENT (A)

The component (a) may include dialkyl quats of various chemical structures, such as dialkyl imidazoline quats, dialkyl ammonium quats, dialkyl amidoamine quats, and others. The component (a) may contain a single dialkyl quat, a mixture of quats of the same general structure with different substitution, or a mixture of different dialkyl quats.

In one embodiment, the dialkyl imidazoline quat is wherein at least a portion of the mixture includes at least one dialkyl imidazoline quat having at least one $C_{20}$–$C_{24}$ alkyl group; the $C_{20-24}$ substitution content of said mixture being from about 10% to about 95% with respect to $C_{10+}$ reference substitution range.

The preferred dialkyl quats are imidazoline quats. In one embodiment, the component (a) may include one or more dialkyl imidazoline quats of the formula (I):

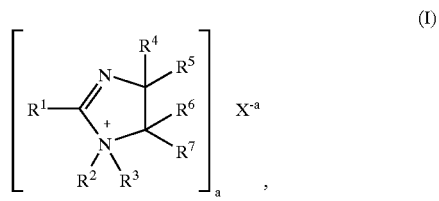

where X is a salt-forming anion, such as chloride, bromide, iodide, fluoride, sulfate, methyl sulfate, methanebenzylsulfonate, phosphate, nitrite, nitrate, carboxylate, or a mixture thereof, preferably, chloride or methyl sulfate; a is the ionic charge of X;

$R^1$, $R^2$, and $R^3$ are independently hydrogen, $C_1$–$C_{30}$ alkyl, $C_1$–$C_{30}$ alkylhydroxy, $C_1$–$C_{30}$ alkyl amido $R_{(C1-C6)}$ wherein $R_{(C1-C6)}$ is a $C_1$–$C_6$ alkylene or benzyl, $C_1$–$C_{30}$ alkylaryl amido $R_{(C1-C6)}$, or $C_1$–$C_{30}$ alkylhydroxy amido $R_{(C1-C6)}$;

two of $R^1$, $R^2$, and $R^3$ are independently $C_{10}$–$C_{30}$ alkyl, $C_{10}$–$C_{30}$ alkylhydroxy, $C_{10}$–$C_{30}$ alkyl amido $R_{(C1-C6)}$, $C_{10}$–$C_{30}$ alkylaryl amido $R_{(C1-C6)}$, or $C_{10}$–$C_{30}$ alkylhydroxy amido $R_{(C1-C6)}$;

the remaining one of $R^1$, $R^2$ and $R^3$ is hydrogen, $C_1$–$C_8$ alkyl, $C_1$–$C_8$ alkylhydroxy, $C_1$–$C_8$ alkyl amido $R_{(C1-C6)}$, $C_1$–$C_8$ alkylaryl amido $R_{(C1-C6)}$, or $C_1$–$C_8$ alkylhydroxy amido $R_{(C1-C6)}$;

$R^4$, $R^5$, $R^6$, and $R^7$, same or different, are independently hydrogen, alkyl, arylalkyl, alkylaryl, halogen, including bromo and chloro, acetoxy, alkylacetoxy, arylacetoxy, carboxy, alkylcarboxy, hydroxy, or alkoxyhydroxy, preferably, $R^4$, $R^5$, $R^6$, and $R^7$, same or different, are hydrogen or $C_1$–$C_8$ alkyl.

Preferably, $R^1$ is $C_{10}$–$C_{30}$ alkyl or alkylhydroxy, more preferably, $C_{14}$–$C_{30}$ alkyl or alkylhydroxy, yet more preferably, $C_{16}$–$C_{30}$ alkyl or alkylhydroxy, yet more preferably, $C_{20}$–$C_{30}$ alkyl or alkylhydroxy;

$R^2$ is $C_1$–$C_6$ alkyl, more preferably, $C_1$–$C_3$ alkyl, yet more preferably, methyl.

$R^3$ is $C_{10}$–$C_{30}$ alkyl amido $R_{(C1-C6)}$, more preferably, $C_{14}$–$C_{30}$ alkyl amido $C_1$–$C_6$ alkylene, yet more preferably, $C_{16}$–$C_{30}$ alkyl amido $C_1$–$C_3$ alkylene, yet more preferably, $C_{20}$–$C_{30}$ alkyl amido $C_1$–$C_3$ alkylene.

The component (a) may contain a single dialkyl imidazoline quat of the formula (I), or a mixture of quats. If the component (a) includes a mixture of the compounds of the formula (I), the mixture may have a defined substituion content.

In one preferred embodiment, the component (a) is a mixture of dialkyl imidazoline quats of the formula (I), wherein the percentage of $C_{16}$–$C_{30}$, preferably, $C_{20}$–$C_{30}$ groups with respect to the total number of $C_{10+}$ groups in the mixture of the component (a) varies from about 10% to about 80%, preferably, from about 15% to about 70%, more preferably, from about 20% to about 65%, yet more preferably, from about 35% to about 60%.

The compounds (1)–(4) are non-limiting examples of the dialkyl quats of the formula (I):

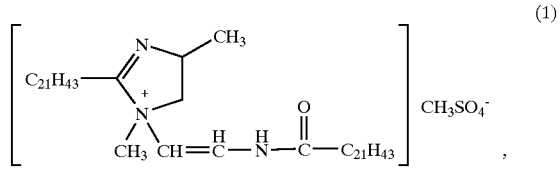

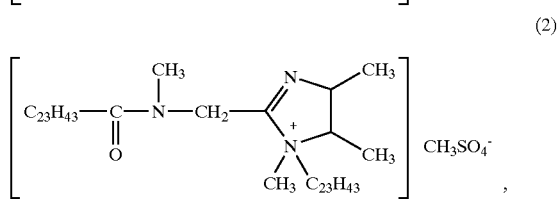

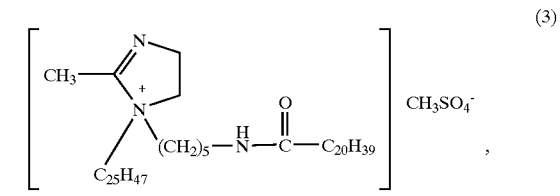

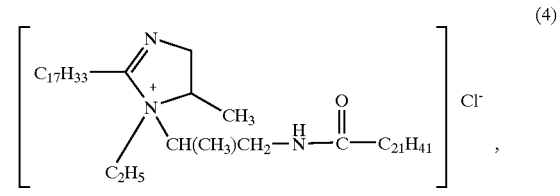

In another non-limiting example, Table 3 shows mixture M4 of dialkyl quats (1), (2), (3), and (4) and the calculation of the mixture's substitution content. The mixture M4 is characterized in terms of its $C_{20-30}$ substitution content (the specified substitution range is $C_{20-30}$ and the reference substitution range is $C_{10+}$).

TABLE 3*

| I | II<br>($N_{20-30}$) | III<br>($P_{20-30}$ = II/2) | IV<br>($M_0$//$M_{10+}$) | V<br>($M_{20-30}$ = III × IV) | VI<br>($S_{20-30}$ = V/IV) |
|---|---|---|---|---|---|
| 1 | 1 | 0.5 | 1 | 0.5 (0.5 × 1) | |
| 2 | 2 | 1 | 2 | 2 (1 × 2) | |
| 3 | 2 | 1 | 2 | 2 (1 × 2) | |
| 4 | 1 | 0.5 | 3 | 1.5 (0.5 × 3) | |
| M4 | | | 8 | 6 | 75% (6/8 × 100%) |

*Explanations for calculating the $C_{20-30}$ content are provided with reference to Table 1.

In another embodiment, the component (a) includes one or more dialkyl imidazoline quats of the formula (II):

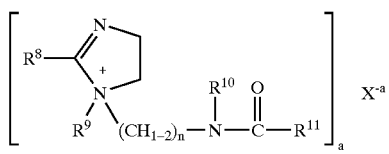

(II)

where X and a are as defined above with reference to the formula (I);

n varies from 1 to 3, preferably, n is 2;

m is 1 or 2, preferably, m is 2;

$R^8$ and $R^{11}$, same or different, are $C_{16}$–$C_{30}$ alkyl, preferably, $C_{16}$–$C_{26}$ alkyl, more preferably, $C_{16}$–$C_{24}$ alkyl, yet more preferably, $C_{20}$–$C_{24}$ alkyl;

$R^9$ is hydrogen or $C_1$–$C_3$ alkyl, preferably, methyl;

$R^{10}$ is hydrogen, alkyl, arylalkyl, alkylaryl, halogen, including bromo and chloro, acetoxy, alkylacetoxy, arylacetoxy, carboxy, alkylcarboxy, hydroxy, or alkoxyhydroxy, preferably, hydrogen or lower alkyl, more preferably, hydrogen.

The particularly preferred compounds of this embodiment have the formula (III):

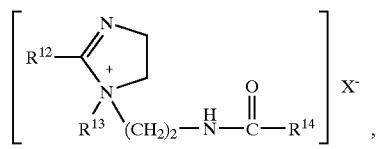

(III)

where X is as defined above; $R^{12}$ and $R^{14}$, same or different, are $C_{16}$–$C_{26}$ alkyl, preferably, $C_{20}$–$C_{24}$ alkyl; and $R^{13}$ is $C_1$–$C_3$ alkyl, preferably, methyl.

The compounds (5)–(8) are examples of dialkyl quats of the formula (II):

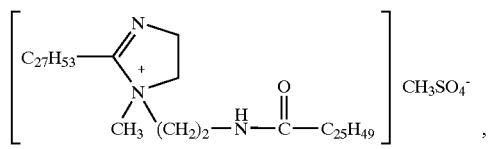

(5)

(6)

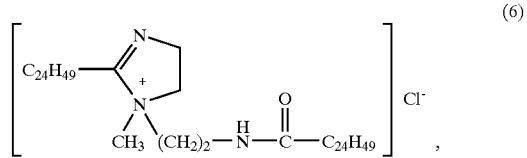

(7)

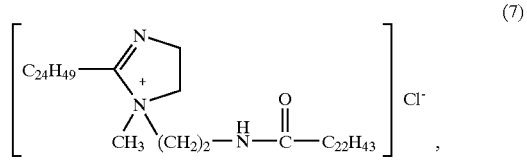

(8)

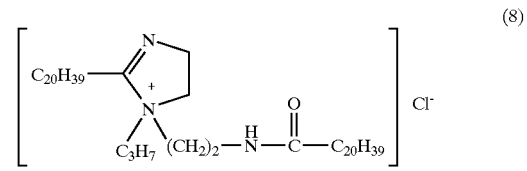

Other on-limiting examples of the quats of the formula (II) are quats (9)–(16) shown in Table 4:

TABLE 4*

| Compound | $R^8$ | $R^{11}$ |
| --- | --- | --- |
| 9  | $C_{18}H_{35}$ | $C_{18}H_{35}$ |
| 10 | $C_{21}H_{40}$ | $C_{22}H_{40}$ |
| 11 | $C_{22}H_{40}$ | $C_{22}H_{40}$ |
| 12 | $C_{16}H_{29}$ | $C_{18}H_{35}$ |
| 13 | $C_{23}H_{40}$ | $C_{23}H_4$ |
| 14 | $C_{18}H_{35}$ | $C_{22}H_{41}$ |
| 15 | $C_{18}H_{33}$ | $C_{18}H_{33}$ |
| 16 | $C_{22}H_{40}$ | $C_{22}H_{40}$ |

*$R^9$ is methyl, $R^{10}$ is hydrogen, m is 2, and n is 2.

In a non-limiting example, Table 5 shows mixture M5 of dialkyl quats (9), (10), and (11) and the calculation of the mixture's substitution content. The mixture M5 is characterized in terms of its $C_{20\text{-}24/16\text{-}30}$ substitution content (the specific range is $C_{20\text{-}24}$ and the reference range is $C_{16\text{-}30}$). The $C_{16\text{-}30}$ range is used as the reference range, instead of the default $C_{10+}$ reference range, since $R^8$ and $R^{11}$ are $C_{16}$–$C_{30}$ alkyl groups. The combined molar content of $R^8$ and $R^{11}$ groups in the mixture M5 is used in the calculations:

TABLE 5

| I (Quat) | II ($N_{20-24}$) | III ($P_{20-24}$ = II/2) | IV ($M_0/M_{10+}$) | V ($M_{20-24}$ = III × IV) | VI ($S_{20-24/16-30}$ = V/IV) |
| --- | --- | --- | --- | --- | --- |
| 9  | 0 | 0 | 1    | 0 (0 × 1) |   |
| 10 | 2 | 1 | 0.75 | 0.75 (0.75 × 1) |   |
| 11 | 2 | 1 | 0.25 | 0.25 (0.25 × 1) |   |
| M5 |   |   | 2    | 1 | 50% (1/2 × 100%) |

Other non-limiting examples of quat mixtures and calculations of their $C_{20-24}$ content are shown in Tables 6 and 7:

TABLE 6

| I (Quat) | II ($N_{20-24}$) | III ($P_{20-24}$ = II/2) | IV ($M_0$// $M_{10+}$) | V ($M_{20-24}$ = III × IV) | VI ($S_{20-24/16-30}$ = V/IV) |
|---|---|---|---|---|---|
| 12 | 0 | 0 | 1 | 0 (0 × 1) | |
| 13 | 2 | 1 | 2.5 | 2.5 (1 × 2.5) | 71.4% |
| M6 | | | 3.5 | 2.5 | (2.5/3.5 × 100%) |

TABLE 7

| I (Quat) | II ($N_{20-24}$) | III ($P_{20-24}$ = II/2) | IV ($M_0$// $M_{10+}$) | V ($M_{20-24}$ = III × IV) | VI ($S_{20-24/16-30}$ = V/IV) |
|---|---|---|---|---|---|
| 14 | 1 | 0.5 | 2 | 1 (0.5 × 2) | |
| 15 | 0 | 0 | 1 | 0 (0 × 1) | |
| 16 | 2 | 1 | 1 | 1 (1 × 1) | |
| M7 | | | 4 | 2 | 50% (2/4 × 100%) | tallow)dimethyl ammonium chloride, di(hydrogenated tallow)dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, and mixtures thereof.

The dialkyl imidazoline quats of the component (a) may be prepared in a number of ways, including methods known to those skilled in the art. Thus, one of suitable preparation methods is described in U.S. Pat. No. 4,855,440, incorporated herein by reference in its entirety. A possible synthetic route involves a reaction of a carboxylic acid, anhydride, or natural or synthetic oil, with a desired dialkyltriamine, followed by quaternization of the resulting imidazoline intermediate.

Reaction Scheme 1 shows an example of the synthetic route for preparation of certain dialkyl imidazoline quats, specifically, 1-methyl-1-(alkyl-acylamido-)ethyl)-2-alkyl immidazolinium methyl sulfates, via a reaction between one mole of diethylene triamine and two moles of a fatty carboxylic acid (or acids), followed by a quaternization with dimethyl sulfate:

Reaction Scheme 1

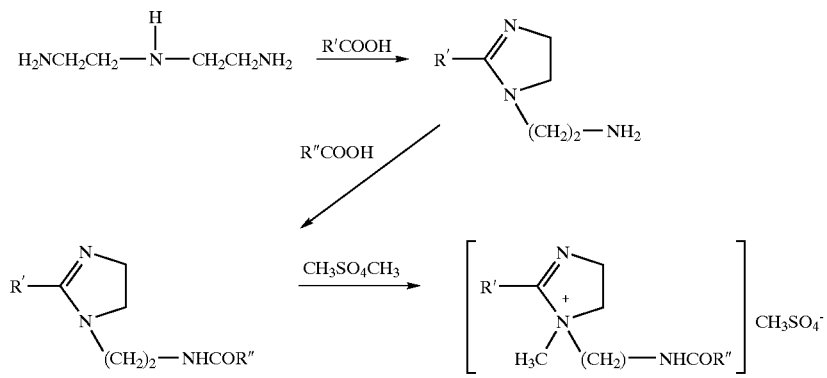

The component (a) may also include other dialkyl quats, for example, dialkyl amidoamine quats described in U.S. patent application Ser. No. 09/409,203, assigned to Croda Incorporated, and incorporated herein by reference herein in its entirety, or dialkyl ammonium quats described in U.S. patent application Ser. No. 09/438,631, also assigned to Croda Incorporated, and incorporated herein by reference herein in its entirety.

Examples of suitable dialkyl ammonium quats are ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof.

Other dialkyl ammonium quats include those wherein the $C_{12}$–$C_{22}$ alkyl is derived from a tallow fatty acid or from a coconut fatty acid. Examples of such ammonium quats include ditallow dimethyl ammonium chloride, ditallow dimethyl ammonium methyl sulfate, di(hydrogenated By varying the starting materials and the reactants, various dialkyl imidazoline quats may be obtained. For example, the carboxylic acids R'COOH and R"COOH may be same or different and may contain a variety of groups R' and R". The nature of R' and R" substitution in the carboxylic acids may be used to vary the R" and R" substituents in the resulting dialkyl imidazoline compounds.

The carboxylic groups R'CO— and R"CO— may be derived from a variety of sources. The carboxylic groups R'CO— and R"CO— may be derived from a variety of sources. Thus, essentially pure carboxylic acids may be used. The suitable carboxylic acids having $C_{18}$–$C_{24}$ alkyl groups include, for example, arachidic ($C^{20}$, including the carboxylic carbon[1], and 0 double bonds in the alkyl group ($C^{20}$:0)), erucic ($C^{22}$:1), behemic ($C^{22}$:0), gadoleic ($C^{20}$:1), erucic ($C^{22}$:1), arachadonic ($C^{20}$:4), culpodonic ($C^{22}$:5) eicosapentaenoic ($C^{20}$:5), docosahexaenoic acid ($C^{22}$:6), tetrcosanoic ($C^{24}$:0); and nervonic ($C^{24}$:1). Other carboxylic acids, including acids having any desirable alkyl substitution may also be used.

[1] Subscripts with reference to the number of carbon atoms indicate the number of carbon atoms without the carboxylic group carbon; the superscripts indicate the number of carbon atoms of the carboxylic group including the carboxylic carbon. Thus, $C^{20}$ is $C_{19}$COO—.

Also, mixtures of carboxylic acids may be used. If a mixture of carboxylic acids is used, the reaction usually provides a corresponding mixture of compounds with R'/R" substitution content similar or identical to the R'/R" distribution in the mixture.

Usually, the use of mixtures of pure carboxylic acids is not economically feasible. Rather, the mixtures of carboxylic acids derived from a single source containing various carboxylic groups, such as natural or synthetic oils, triglycerides, and the like, are typically used. For example, such mixtures may be obtained in commercial quantities via saponification of ester-containing natural or synthetic substances.

In fact, carboxylic acids may be directly replaced in the reactions above by ester-containing natural or synthetic oil or a similar substance. Similarly to the use of carboxylic acid mixtures, the reaction between the ester-containing oil and a triamine usually provides a mixture of compounds with R'/R" substitution content similar or identical to the R'/R" distribution in the oil.

Preferably, the component (a) contains compounds derived from natural and synthetic oils, fatty acids and/or triglycerides.

Thus, the component (a) of the composition of the invention may include a product(s) of a reaction between a compound of the formula

where R' is $C_1-C_{10}$ alkylene, preferably —$CH_2CH_2$— group, and R" is $C_1-C_{10}$ alkylene, preferably, —$CH_2CH_2$- alkylene; and a mixture of natural or synthetic oil-derived carboxylic acids or a natural or synthetic oil.

The suitable oils that may be used directly or provide oil-derived mixtures of carboxylic acids include, for example, HEAR oil, cod liver oil, herring oil, menhaden oil, mustard seed oil, pilchard oil, hear oil, salmon oil, sardine oil and shark liver oil. Of course, other oils and similar substances may also be used. For listing of such substances, please see 1 "Bailey's Industrial Oil and Fat Products" (Daniel Swern, John Wiley & Sons, 4th Ed. 1979), at pages 416–417, 447, 449–450, and 452, which are hereby incorporated by reference.

Table 8 shows approximate percentages of some of the $C^{20}+$ (including the carboxylic carbon) components in some of the common oils:

The particularly preferred oil is HEAR oil, especially high erucic rapeseed oil, which typically contains 46% of $C^{22}:1$ alkyl (erucic), 1.5% of $C^{22}:0$ alkyl (behemic), and 11% of $C^{20}:1$ alkyl (gadoleic) by weight.

COMPONENT (B)

The component (b) may include monoalkyl quats of various chemical structures, such as monoalkyl imidazoline quats, monoalkyl ammonium quats, monoalkyl amidoamine quats, and others. The component (b) may contain a single monoalkyl quat, a mixture of quats of the same general structure with different substitution, or a mixture of different monoalkyl quats.

The preferred quats are monoalkyl imidazoline quats and monoalkyl ammonium quats. The most preferred quats are monoalkyl imidazoline quats. In one embodiment, the component (b) may include one or more monoalkyl imidazoline quats of the formula (IV):

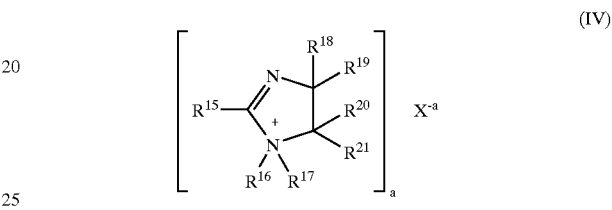

where X is a salt-forming anion, such as chloride, bromide, iodide, fluoride, sulfate, methyl sulfate, methanebenzylsulfonate, phosphate, nitrite, nitrate, carboxylate, or a mixture thereof, preferably, chloride or methyl sulfate; a is the ionic charge of X;

$R^{15}$, $R^{16}$ and $R^{17}$ are independently hydrogen, $C_1-C_{30}$ alkyl, $C_1-C_{30}$ alkylhydroxy, $C_1-C_{30}$ alkyl amido $R_{C1-C6}$, $C_1-C_{30}$ alkylaryl amido $R_{C1-C6}$, or $C_1-C_{30}$ alkylhydroxy amido $R_{C1-C6}$, wherein $R_{C1-C6}$ is a $C_1-C_6$ alkylene or benzyl;

one of $R^{15}$, $R^{16}$ and $R^{17}$ is independently $C_1-C_{30}$ alkyl, $C_{10}-C_{30}$ alkylhydroxy, $C_{10}-C_{30}$ alkyl amido $R_{C1-C6}$, $C_{10}-C_{30}$ alkylaryl amido $R_{C1-C6}$, or $C_{10}-C_{30}$ alkylhydroxy amido $R_{C1-C6}$;

the remaining two of $R^{15}$, $R^{16}$ and $R^{17}$ are independently hydrogen, $C_1-C_8$ alkyl, $C_1-C_8$ alkylhydroxy, $C_1-C_8$ alkyl amido $R_{C1-C6}$, $C_1-C_8$ alkylaryl amido $R_{C1}C_6$, or $C_1-C_8$ alkylhydroxy amido $R_{C1-C6}$;

preferably, $R^{15}$ is $C_{10}-C_{30}$ alkyl or alkylhydroxy, more preferably, $C_{14}-C_{30}$ alkyl or alkylhydroxy, yet more preferably, $R^{15}$ is $C_{16}-C_{30}$ alkyl or alkylhydroxy, yet more preferably, $R^{15}$ is $C_{20}-C_{30}$ alkyl or alkylhydroxy;

$R^{16}$ is $C_1-C_6$ alkyl, more preferably, $C_1-C_3$ alkyl, yet more preferably, methyl;

TABLE 8

| Substance | $C^{20}:0$ | $C^{20}:1$ | $C^{20}:4$ | $C^{20}:5$ | $C^{22}:0$ | $C^{22}:1$ | $C^{22}:5$ | $C^{22}:6$ | $C^{24}:0$ |
|---|---|---|---|---|---|---|---|---|---|
| Cod liver oil | 8.8–14.6% | | | 2.6–9% | | 4.6–13.3% | 1–2% | 8.6–19% | |
| Herring oil | | 1.5–19.2% | | 4.6–10.2% | | 2.8–19.9% | 1–3.7% | 3.8–24.1% | |
| Menhaden oil | | 0.9–2.7% | 0.6–1.2% | 10.2–13.5% | | 0.7–1.7% | 1.1–2.3% | 3.3–14% | |
| Pilchard (Sardine) oil | | 3.2% | 1.6% | 16.9% | | 3.6% | 2.5% | 12.9% | |
| HEAR oil | | 0.8–13.5% | | | | 20.1–59.4% | | | 0.1–1.4% |
| Mustard Seed oil | | 7% | | | | 44.2% | | | |

The oils shown in Table 7 generally contain from about 30% to about 90% of $C_{20}-C_{30}$ alkyl groups in their fatty carboxylic groups. The oils often exhibit substantial variations in $C_{20}-C_{30}$ content, and also include some $C_1-C_{19}$ alkyl content.

$R^{17}$ is $C_1-C_8$ alkyl, $C_1-C_8$ alkylhydroxy, $C_1-C_8$ alkyl amido $R_{C1-C6}$, or $C_1-C_8$ alkylhydroxy amido $R_{C1-C6}$, more preferably, $C_1-C_8$ alkyl amido $C_1-C_3$ alkylene or $C_1-C_8$ alkylhydroxy;

$R^{18}$, $R^{19}$, $R^{20}$, and $R^{21}$, same or different, are independently hydrogen, alkyl, arylalkyl, alkylaryl, halogen, including bromo and chloro, acetoxy, alkylacetoxy, arylacetoxy, carboxy, alkylcarboxy, hydroxy, or alkoxyhydroxy; preferably, $R^{18}$, $R^{19}$, $R^{20}$, and $R^{21}$, same or different, are hydrogen or $C_1$–$C_8$ alkyl.

Compounds (17)–(19) are non-limiting examples of monoalkyl quats of the formula (IV):

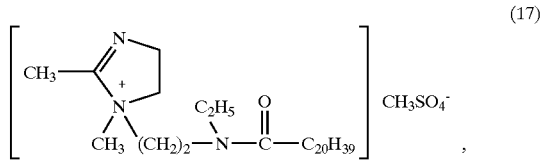
(17)

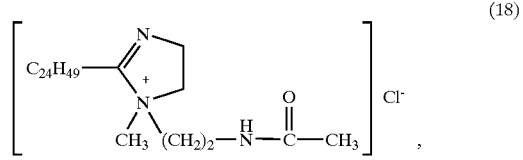
(18)

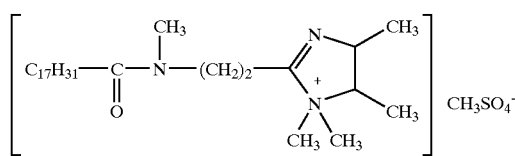
(19)

The component (b) may include a single compound of the formula (IV), or a mixture of such compounds. If the component (b) includes a mixture of the compounds of the formula (IV), the mixture may have a defined substitution content. As described in reference to dialkyl quats of the component (a), the substitution content of the mixtures is measured as a percentage ratio of a total number of substituents within a specified range to a total number of substituents within a broader reference range.

The component (b) may be a mixture of monoalkyl imidazoline quats, at least one of which has a $C_{16}$–$C_{30}$ alkyl group; the $C_{16\text{-}30}$ substitution content of the mixture being from about 10% to about 95%, preferably, from about 15% to about 85%, more preferably, from about 20% to about 80%, yet more preferably, from about 25% to about 75%.

Other non-limiting examples of monoalkyl quats of the formula (V) are quats (24)–(28) shown in Table 8:

TABLE 8*

| Quat | $R^{22}$ |
|---|---|
| 24 | $C_{18}H_{35}$ |
| 25 | $C_{21}H_{40}$ |
| 26 | $C_{22}H_{41}$ |
| 27 | $C_{18}H_{33}$ |
| 28 | $C_{22}H_{40}$ |

*$R^{23}$ is $CH_3$, $R^{24}$ is hydrogen, $R^{25}$ is $CH_3$

In non-limiting examples, Tables 9 and 10 show mixtures M8 and M9, respectively, of quats (24)–(28) and the calculations of their substitution content. Both mixtures are characterized in terms of their $C_{20\text{-}24}$ content (the specified range is $C_{20\text{-}24}$ and the reference range is $C_{10+}$).

TABLE 9*

| I (Quat) | II ($N_{20-24}$) | IV ($M_0//M_{10+}$) | V ($M_{20-20}$ = II × IV) | VI ($S_{20-24}$ = V/IV) |
|---|---|---|---|---|
| 24 | 0 | 1 | 0 (0 × 1) | |
| 25 | 1 | 1.5 | 1.5 (1 × 1.5) | |
| M8 | | 2.5 | 1.5 | 60% (1.5/2.5 × 100%) |

*$N_{10+}$ is 1; column (III) is omitted

TABLE 10*

| I (Quat) | II ($N_{20-4}$) | IV ($M_0//M_{10+}$) | V ($M_{20-24}$ = II × IV) | VI ($S_{20-24}$ = V/IV) |
|---|---|---|---|---|
| 26 | 1 | 2 | 2 (1 × 2) | |
| 27 | 0 | 1 | 0 (0 × 1) | |
| 28 | 1 | 1 | 1 (1 × 1) | |
| M9 | | 4 | 3 | 75% (3/4) × 100% |

In another embodiment, the component (b) includes one or more monoalkyl imidazoline compounds of the formula (V):

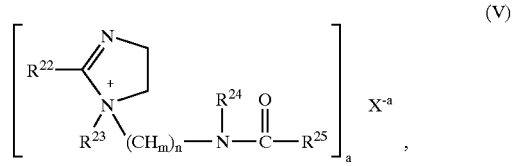
(V)

where X and a are as defined above with reference to the formula (IV);

$R^{22}$ is $C_{16}$–$C_{30}$ alkyl, preferably, $C_{16}$–$C_{26}$ alkyl, more preferably, $C_{16}$–$C_{24}$ alkyl;

$R^{23}$ is hydrogen or $C_1$–$C_3$ alkyl;

$R^{24}$ is hydrogen, alkyl, arylalkyl, alkylaryl, halogen, including bromo and chloro, acetoxy, alkylacetoxy, arylacetoxy, carboxy, alkylcarboxy, hydroxy, or alkoxyhydroxy, preferably, hydrogen or lower alkyl, more preferably, hydrogen;

$R^{25}$ is $C_1$–$C_8$ alkyl or $C_1$–$C_8$ alkylhydroxy;

n varies from 1 to 3, preferably, n is 2; and m is 1 or 2, preferably, m is 2; or compounds of the formula (VI):

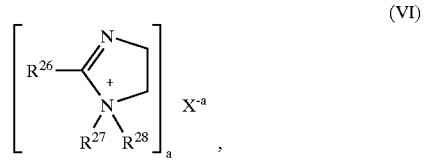
(VI)

where X and a are as defined above with reference to the formula (IV);

$R^{26}$ is $C_{16}$–$C_{30}$ alkyl, preferably, $C_{16}$–$C_{26}$ alkyl, more preferably, $C_{16}$–$C_{24}$ alkyl;

$R^{27}$ is hydrogen or $C_1$–$C_3$ alkyl;

$R^{28}$ are $C_1$–$C_8$ alkyl or $C_1$–$C_8$ alkylhydroxy;

n varies from 1 to 3, preferably, n is 2; and m is 1 or 2, preferably, m is 2.

Compounds (20) and (21) are non-limiting examples of monoalkyl quats of the formula (V):

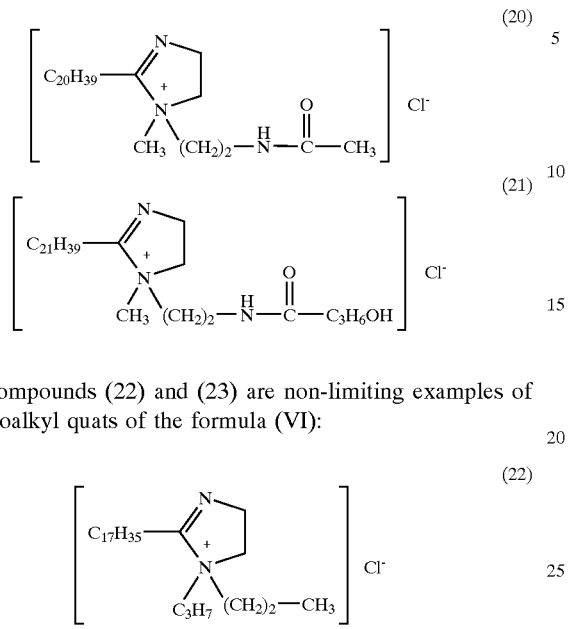

Compounds (22) and (23) are non-limiting examples of monoalkyl quats of the formula (VI):

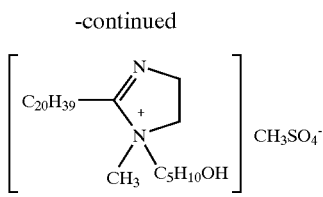

-continued

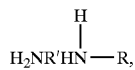

The monoalkyl quats may be prepared in a number of ways, including methods known to those skilled in the art. For example, the compounds of the invention may be prepared via a reaction of a carboxylic acid, anhydride, or natural or synthetic oil, with a desired N-alkyl-N-alkylamino-diamine, followed by quaternization of the resulting imidazoline intermediate.

Reaction Scheme 2 shows an example of the synthetic route for preparation of certain monoalkyl imidazoline quats, specifically, 1-methyl-1-(lower alkyl)-2-alkyl imidazolinium chlorides, via a reaction between N-lower alkyl-N-ethyleneamino diamine and a fatty carboxylic acid(s), followed by a quaternization with methyl chloride:

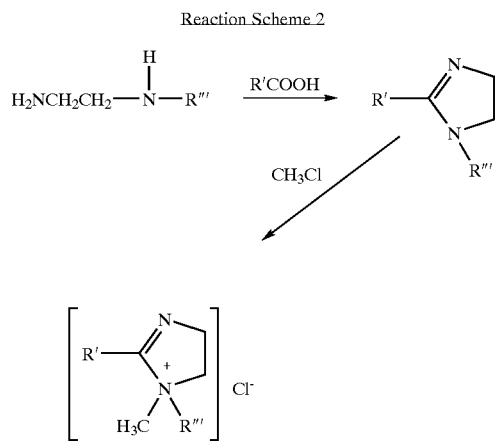

By varying the starting materials and the reactants, other imidazoline quaternary compounds may be obtained. For example, if R''' is alkylhydroxy (e.g., —CH$_2$CH$_2$CH$_2$OH), the resulting monoalkyl quat includes an alkylhydroxy group:

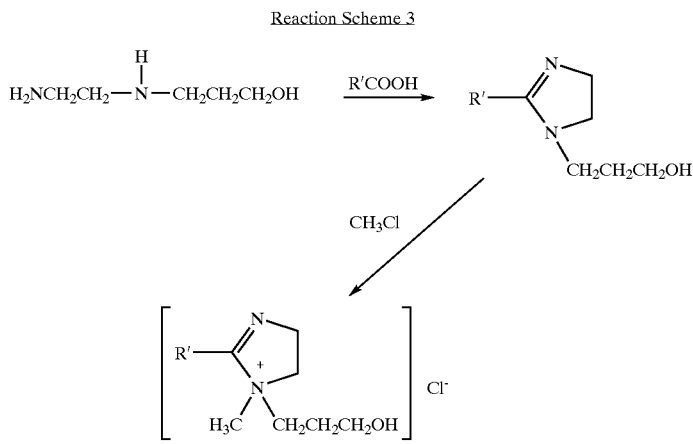

Thus, the component (b) of the composition of the invention may include a product(s) of a reaction between
(a) a compound of the formula $$H_2NR'HN—R,$$

where R' is C$_1$–C$_3$ alkylene, preferably —CH$_2$CH$_2$— group, and R is C$_1$–C$_8$ alkyl, C$_1$–C$_8$ alkylhydroxy, or benzyl; and
(b) a mixture of natural or synthetic oil-derived carboxylic acids or a natural or synthetic oil.

The carboxylic group of monoalkyl imidazoline quats may be derived from any of the sources described with reference to dialkyl imidazoline quats. The preferred source is also HEAR oil.

In another embodiment, the component (b) may include monoalkyl ammonium quats of the formula

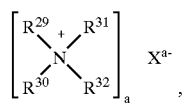

where X and a are as defined above; $R^{29}$ is $C_{10}$–$C_{30}$ alkyl, $C_{10}$–$C_{30}$ alkylaryl, $C_{10}$–$C_{30}$ arylalkyl or $C_{10}$–$C_{30}$ alkylhydroxy; and $R^{30}$, $R^{31}$, and $R^{32}$, same or different, are independently hydrogen, $C_1$–$C_8$ alkyl or $C_1$–$C_8$ alkylhydroxy.

Examples of monoalkyl ammonium quats include cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, and lauryl dimethyl ammonium chloride. Yet other suitable ammonium quats are stearamidopropyl PG-dimonium chloride phosphate, stearamidopropyl ethyldimonium ethosulfate, stearamidopropyl dimethyl(myristyl acetate)ammonium chloride, stearamidopropyl dimethyl cetearyl ammonium tosylate, stearamidopropyl dimethyl ammonium chloride, stearamidopropyl dimethyl ammonium lactate, and mixtures thereof.

In general, a producer provides raw quats to manufacturers of personal care and cosmetic products, who formulate them in the final products. An important characteristic of raw quats, as well as the final products that incorporate them, is the so-called cationic activity, which measures a concentration of positive charges in a substance, product, etc. The cationic activity may be measured by several methods readily understood by those skilled in the art. One such method utilizes a standardized solution of an anionic material, such as sodium lauryl sulfate. This material is added to the solution containing the quat until full complexation of the quat's cations (the end point) has been reached. The end point can be measured potentiometrically or by the use of color indicators.

Typical tests involve titrating a sample of the quat, usually dissolved in a solvent, with the standardized solution of sodium lauryl sulfate until the endpoint is reached. As described in the co-pending and co-assigned U.S. patent application Ser. No. 09/438,631, incorporated by reference herein in its entirety, once the endpoint is reached, the cationic activity can be calculated according to the following formula:

$$\% \text{ cationic activity} = \frac{mL \times N \times MW \times 100}{S.wt. \times 1000}$$

Where:
mL=the number of mL of anionic material
N=the normality of the solution used
MW=the molecular weight of the quat being analyzed
S.wt.=the sample weight in grams For additional information regarding the methodology for measuring the cationic activity, see W. Schempp and H. T. Trau, Wochenblatt fur Papierfabrikation 19, 1981, pages 726–732; or J. P. Fischer and K. Lohr, Organic Coatings Science Technology, Volume 8, pages 227–249, Marcel Dekker, Inc. (April 1986), both incorporated herein by reference in their entirety.

It is desirable to provide raw quats in a concentrated form with high cationic activity, as a solid or semi-solid solution or dispersion. Without wishing to be bound by any specific theory, it is believed that a desired amount of a given quat or mixture of quats to be placed in a formulation may be measured by the cationic activity of the quat raw material. The quat raw materials with high cationic activity permit better transportation efficiency since they occupy smaller space while providing the same desired quat amounts. It is also desirable to produce raw quats that, in addition to having high cationic activity, provide for ease in commercial handling and storage. For example, the raw quat that melt at lower temperatures minimize quat decomposition and improve energy efficiency. For this purpose, it is preferred for the raw quats to be flakeable or pastillatable.

Thus, in accordance with another aspect, the invention also provides compositions in the form of concentrated, usually solid, solutions or suspensions of components (a) and (b) in a suitable carrier. Such compositions are called herein quats raw materials. The preferred carrier is a solvent, and the preferred solvents include isopropyl alcohol, SDA-40, propylene glycol, butylenes glycol, various fatty alcohols, and mixtures thereof.

Preferably, the quat raw materials of the invention are flakeable or pastillatable solids with high quat cationic activity. The quat cationic activity is the cationic activity that is attributed to quaternary nitrogen compounds.

The preferred total quat cationic activity of quat raw materials of the invention is greater than 10%, preferably, greater than 20%, more preferably, greater than 35%, yet more preferably, greater than 50%. With respect to relative contributions of the components (a) and (b), preferably, the component (a) provides from about 20% to about 90%, and the component (b) provides from about 10% to about 75%, of the total quat cationic activity in the raw material. The quat raw materials of the invention may also include one or more desirable ingredients of final cosmetic/personal care formulations, such as emollients and the like, as well as various impurities. The list of such ingredients may be found below.

In accordance with another aspect, the invention also provides compositions in the form of various cosmetic and/or personal care products. In such form, the compositions of the invention include components (a), and (b), and may include various other ingredients, such as active and additional ingredients, both conventional and otherwise. Such compositions may be referred to as final product compositions, and may be in the form of, for example, sunscreen compositions for hair and/or skin, such as lotions, gels, sprays, and the like, hand cleaners, bath compositions, suntan oils, antiperspirant compositions, perfumes and colognes, cold creams, pre-shaves, deodorants, topical pharmaceutical ointments, skin moisturizers, facial cleansers, cleansing creams, skin gels, shampoos, hair conditioners, detergents, household cleaning products, make-up products, lipstick products, mascara, and hair coloring products. The preferred final product compositions of the invention are compositions for treating human hair, such as shampoos or conditioners.

The final product compositions of the invention, including preparations for skin and hair, include components (a), and (b) described herein. The total amount of components (a) and (b) in the products depend on the specific application, and may vary from about 0.1% to about 40%, more preferably, from about 0.1% to about 10%, yet more preferably, from about 0.5% to about 2% by the weight of the product composition. However, different amounts of quat mixtures may be preferred depending on the nature of the product.

The final product compositions that include components (a) and (b) may be in the form of liquids, gels, creams, emulsions, foams, and solids; may be clear or opaque; and may be formulated as aqueous and non-aqueous preparations, including but not limited to topical preparations. Preferably, the final product compositions are dispersions or solutions in water, or in a mixture of water with a suitable secondary solvent. Suitable inert solvents include various lower alkanols and glycols. Lower alkanols having from one to four carbon atoms are suitable for use with the present invention, and lower alkanols having from two to three carbon atoms are preferred. Glycols having from three to eight carbon atoms are suitable for use with the present invention, while glycols having from three to six carbon atoms are preferred. Examples of suitable lower alkanols and glycols include methanol, ethanol, isopropanol, butanol, hexylene glycol, 1,3-butylene glycol, 1,2- and 1,3-propane diol, 2-methyl 1,3-propane diol, propylene glycol, diethylene glycol, and the like. The total amount of solvent may be up to about 98% by weight of the composition, preferably, from about 20% to about 90%, more preferably, from about 50% to about 90% by weight of the composition. Again, however, different amounts of solvent may be preferred depending on the nature of the product. If a mixture of water and a secondary solvent is used, the secondary solvent may be present in the amount of up to 90%, preferably, between about 25% and about 80% by weight of water in the composition.

It is believed that imidazoline quat and/or quat mixtures improves hair substantivity of hydrophobic ingredients of cosmetic and personal care products, which is typically thought of as the degree of deposition of the hydrophobic ingredient on hair and is desirable. The hydrophobic components are those that are substantially insoluble in water. Typically, such hydrophobic ingredients are soluble in oils. Thus, the compositions described herein may further include at least one hydrophobic ingredient, examples of which include botanical extracts, vitamin E, vitamin A, silicones, waxes and antioxidants.

In addition to components (a), and (b), the compositions of the invention may include various active and additional ingredients, both conventional and otherwise. Of course, a decision to include an ingredient and the choice of specific active and additional ingredients depends on the specific application and product formulation. Also, the line of demarcation between an "active" ingredient and an "additional ingredient" is artificial and dependent on the specific application and product type. A substance that is an "active" ingredient in one application or product may be an "additional" ingredient in another, and vice versa.

Thus, the compositions of the invention may include one or more active ingredients, which provide some benefit to the object of the application of the composition, for example, hair or skin. Such active ingredients may include one or more substances such as cleaning agents, hair conditioning agents, skin conditioning agents, hair styling agents, antidandruff agents, hair growth promoters, perfumes, sunscreen compounds, pigments, moisturizers, film formers, hair colors, make-up agents, detergents, thickening agents, emulsifiers, antiseptic agents, deodorant actives and surfactants.

The choice of the active ingredients depends on the nature of the desired cosmetic or personal care product. For example, the sunscreen compounds may be used in the sunscreen lotions, shampoos, hair care lotions and the like. For each type of active ingredient, one or more compounds may be present. Likewise, more than one type of active ingredient may be present.

SURFACTANTS

In addition to components (a) and (b), other surfactants may be present in the compositions of the invention, including one or more nonionic surfactants, anionic surfactants, cationic surfactants, amphoteric surfactants, zwitterionic surfactants, and mixtures thereof. For some of surfactants that may be used in combination with the compositions of the invention, please see McCutcheon's, Detergents and Emulsifiers, (1986), U.S. Pat. Nos. 5,151,210, 5,151,209, 5,120,532, 5,011,681, 4,788,006, 4,741,855, 4,704,272, 4,557,853, 4,421,769, 3,755,560; all incorporated herein by reference in their entirety. The total amounts of surfactants in the composition may vary from 1 to 75%, depending on the nature of specific product.

CATIONIC SURFACTANTS

The components (a) and (b) are cationic surfactants suitable for use in various personal care products, especially hair care products such as conditioners and shampoos. In addition, other cationic surfactants may be present in the compositions of the invention. The amounts and the nature of cationic surfactants present in the compositions of the invention depend on the nature of the composition. In the final product composition, the total amount of cationic surfactants, including the components (a) and (b) described herein, may vary from 0.1% to about 40%, more preferably, from about 0.1% to about 15%, yet more preferably, from about 0.5% to about 2% by the weight of the product composition. However, different amounts of cationic surfactants may be preferred depending on the nature of the product. Suitable additional cationic surfactants are disclosed in McCutcheon, Detergents & Emulsifiers, (M.C. Publishing Co. 1979); U.S. Pat. Nos. 3,155,591, 3,929,678, 3,959,461, 4,387,090, which are incorporated by reference herein.

FATTY AMINES

The compositions of the invention may also include salts of primary, secondary and tertiary $C_{12}$–$C_{22}$ amines. Examples of such suitable amines include stearamido propyl dimethyl amine, diethyl amino ethyl stearamide, dimethyl stearamine, dimethyl soyamine, soyamine, tri(decyl)amine, ethyl stearylamine, ethoxylated stearylamine, dihydroxyethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Some cationic amine surfactants useful in the compositions of the present invention are disclosed in U.S. Pat. No. 4,275,055, incorporated by reference herein.

AMIDOAMINES

The compositions of the invention may also include aminoamides, such as disclosed in U.S. patent application Ser. No. 09/409,203, assigned to Croda Inc., and incorporated by reference herein.

NON-IONIC SURFACTANTS

The compositions of the invention may also include various non-ionic surfactants. Among the suitable nonionic surfactants are condensation products of $C_8$–$C_{30}$ alcohols with sugar or starch polymers. These compounds can be represented by the formula $(S)_n$—O—R, wherein S is a sugar moiety such as glucose, fructose, mannose, and galactose; n is an integer of from about 1 to about 1000, and R is $C_8$–$C_{30}$ alkyl. Examples of suitable $C_8$–$C_{30}$ alcohols from which the R group may be derived include decyl alcohol, cetyl alcohol, stearyl alcohol, lauryl alcohol, myristyl alcohol, oleyl alcohol, and the like. Specific examples of these surfactants include decyl polyglucoside and lauryl polyglucoside.

Other suitable nonionic surfactants include the condensation products of alkylene oxides with fatty acids (i.e., alkylene oxide esters of fatty acids). These materials have the general formula $RCO(X)_nOH$, wherein R is a $C_{10}$–$C_{30}$ alkyl, X is —$OCH_2CH_2$— (derived from ethylene oxide) or —$OCH_2CHCH_3$— (derived from propylene oxide), and n is an integer from about 1 to about 200.

Yet other suitable nonionic surfactants are the condensation products of alkylene oxides with fatty acids (i.e., alkylene oxide diesters of fatty acids) having the formula $RCO(X)_nOOCR$, wherein R is a $C_{10}$–$C_{30}$ alkyl, X is —$OCH_2CH_2$— (derived from ethylene oxide) or —$OCH_2CHCH_3$— (derived from propylene oxide), and n is an integer from about 1 to about 200.

Yet other nonionic surfactants are the condensation products of alkylene oxides with fatty alcohols (i.e., alkylene oxide ethers of fatty alcohols) having the general formula $R(X)_nOR'$, wherein R is $C_{10}$–$C_{30}$ alkyl, n is an integer from about 1 to about 200, and R' is H or a $C_{10}$–$C_{30}$ alkyl.

Still other nonionic surfactants are the compounds having the formula $RCO(X)_nOR'$ wherein R and R' are $C_{10}$–$C_{30}$ alkyl, X is —$OCH_2CH_2$— (derived from ethylene oxide) or —$OCH_2CHCH_3$— (derived from propylene oxide), and n is an integer from about 1 to about 200.

Examples of alkylene oxide-derived nonionic surfactants include ceteth-1, ceteth-2, ceteth-6, ceteth-10, ceteth-12, ceteraeth-2, ceteareth6, ceteareth-10, ceteareth-12, steareth-1, steareth-2, stearteth-6, steareth-10, steareth-12, PEG-2 stearate, PEG4 stearate, PEG6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amides disclosed, for example, in U.S. Pat. Nos. 2,965,576, 2,703,798, and 1,985,424, which are incorporated herein by reference.

ANIONIC SURFACTANTS

The compositions of the invention may also include various anionic surfactants. Several examples of suitable anionic surfactants are disclosed in U.S. Pat. No. 3,929,678, which is incorporated herein by reference. Further examples of suitable anionic surfactants include alkoyl isethionates, and alkyl ether sulfates.

The alkoyl isethionates typically have the formula $RCO$—$OCH_2CH_2$—$SO_3M$, wherein R is $C_{10}$–$C_{30}$ alkyl, and M is a water-soluble cation, such as ammonium, sodium, potassium, or triethanolamine. The examples of suitable isethionates include ammonium cocoyl isethionate, sodium cocoyl isethionate, sodium lauroyl isethionate, sodium stearoyl isethionate, and mixtures thereof. Preferred for used herein are ammonium cocoyl isethionate, sodium cocoyl isethionate, and mixtures thereof.

The alkyl ether sulfates typically have the formulas $ROSO_3M$ and $RO(C_2H_4O)_xSO_3M$, where R is $C_{10}$–$C_{30}$ alkyl, x varies from about 1 to about 10, and M is a water-soluble cation such as ammonium, sodium, potassium and triethanolamine.

Yet another suitable class of anionic surfactants are alkali metal salts of $C_8$–$C_{30}$ carboxylic acids and alkylsulfonates of the formula $R_1$—$SO_3M$ (where $R_1$ is $C_8$–$C_{30}$ alkyl; preferably, $C_{12}$–$C_{22}$ alkyl, and M is a cation), including succinamates, and $C_{12}$–$C_{24}$ olefin sulfonates and carboxylates.

AMPHOTERIC SURFACTANTS

The compositions of the invention may also include zwitterionic and amphoteric surfactants. Suitable amphoteric and zwitterionic surfactants are, for example, derivatives of mono- or di-$C_8$–$C_{24}$ secondary and tertiary amines, such as alkyl imino acetates, carboxylates, sulfonates, sulfates, phosphates, and phosphonates, including iminodialkanoates and aminoalkanoates of the formulas $RN(CH_2)_mCO_2M_2$ and $RNH(CH_2)_mCO_2M$, where m varies from 1 to 4, R is $C_8$–$C_{30}$ alkyl; preferably, $C_{12}$–$C_{22}$ alkyl, and M is H, alkali metal, alkaline earth metal ammonium, or alkanolammonium.

Other suitable amphoteric and zwitterionic surfactants are imidazolinium and ammonium derivates. Suitable examples of such amphoteric surfactants include sodium 3-dodecyl-aminopropionate, sodium 3-dodecylaminopropane sulfonate, N-alkyltaurines; N-higher alkyl aspartic acids, and coamidopropyl PG-dimonium chloride phosphate. For further examples of suitable amphoteric and zwitterionic surfactants, please see U.S. Pat. Nos. 2,658,072, 2,438,091, and 2,528,378, which are incorporated herein by reference Yet other suitable amphoteric and zwitterionic surfactants are betaines. Examples of suitable betaines include coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine, and amidobetaines and amidosulfobetaines, oleyl betaine, and cocamidopropyl betaine.

SUNSCREEN COMPOUNDS

A wide variety of sunscreen compounds are suitable for use with the compositions of the present invention. Depending on the nature of the composition, the sunscreen compounds may be added in the amount of up to about 40% by weight of the composition, preferably, from about 1% to about 30%. However, the preferred amount may vary depending on the nature of the composition. Thus, for the final product compositions in the form of a shampoo or conditioner, the suitable sunscreen agent may be included in the amount of up to about 40% by weight of the composition, preferably, from about 0.5% to about 5%, more preferably, from about 05 to about 1.5% by weight of the composition. Suitable sunscreen compounds include, for example, p-aminobenzoic acid, its salts and its derivatives; anthranilates; salicylates; cinnamic acid derivatives; dihydroxycinnamic acid derivatives; trihydroxycinnamic acid derivatives; hydrocarbons; dibenzalacetone and benzalacetophenone; naphtholsulfonates; dihydroxy-naphtholic acid and its salts; coumarin derivatives; diazoles; quinine salts; quinoline derivatives; hydroxy- or methoxy-substituted benzophenones; uric and vilouric acids; tannic acid and its derivatives; hydroquinone; amino benzoates, salicylates, ferrulic acid derivatives, phenylbenzimidazole sulfonic acids, benzophenone sulfonic acids, thioctic acids derivatives, oil-soluble cinnamates, and benzophenones. For other suitable sunscreen compounds, please see Segarin, et al., Cosmetics Science and Technology, Chapter VIII, pages 189 et seq., incorporated herein by reference.

Specific suitable sunscreen compounds include 2-ethylhexyl p-methoxycinnamate, 4,4'-t-butyl methoxydibenzoylmethane, 2-hydroxy-4- methoxybenzophenone, octyldimethyl p-aminobenzoic acid, digalloyltrioleate, 2,2-dihydroxy-4-methoxybenzophenone, ethyl-4->bis(hydroxypropyl)!-aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl p-dimethylaminobenzoate, 2-phenylbenzimidazole-5-sulfonic acid, 2-(p-dimethyl-aminophenyl)-5-sulfonicbenzoxazoic acid, para-aminobenzoic acid, benzophenone-1, benzophenone-1, benzophenone-2, benzophenone-3, benzophenone-4, benzophenone-5, benzophenone-6, benzophenone-8, benzophenone-12, methoxycinnamate, avobenzone, ethyl dihydroxypropyl para-aminobenzoate, glyceryl para-aminobenzoate, methyl anthranilate, octocrylene, octyl dimethyl para-aminobenzoate, octyl methoxycinnamate, octyl salicylate, zinc oxide, titanium dioxide, and red petrolatum.

EMOLLIENTS

The compositions of the invention may also include one or emollient compounds such as fats, waxes, lipids, silicones, hydrocarbons, fatty alcohols and a wide variety of solvent materials. The amount of the emollient depends on the application. For the final product compositions, emmollinets are included in the amount of up to 50% by weight of the composition, preferably, from about 0.1% to about 20%, and more preferably, from about 0.5% to about 10% by weight of the composition.

Examples of suitable emollients include $C_{8-30}$ alkyl esters of $C_{8-30}$ carboxylic acids; $C_{1-6}$ diol monoesters and diesters of $C_{8-30}$ carboxylic acids; monoglycerides, diglycerides, and triglycerides of $C_{8-30}$ carboxylic acids, cholesterol esters of $C_{8-30}$ carboxylic acids, cholesterol, and hydrocarbons. Examples of these materials include diisopropyl adipate, isopropyl myristate, isopropyl palmitate, ethylhexyl palmitate, isodecyl neopentanoate, $C_{12-15}$ alcohols benzoates, diethylhexyl maleate, PPG-14 butyl ether, PPG-2 myristyl ether propionate, cetyl ricinoleate, cholesterol stearate, cholesterol isosterate, cholesterol acetate, jojoba oil, cocoa butter, shea butter, lanolin, lanolin esters, mineral oil, petrolatum, and straight and branched $C_{16}$–$C_{30}$ hydrocarbons.

Also useful are straight and branched chain fatty $C_8$–$C_{30}$ alcohols, for example, stearyl alcohol, isostearyl alcohol, ehenyl alcohol, cetyl alcohol, isocetyl alcohol, and mixtures thereof. Examples of other suitable emollients are disclosed in U.S. Pat. No. 4,919,934; which is incorporated herein by reference in its entirety.

Other suitable emollients are various alkoxylated ethers, diethers, esters, diesters, and trimesters. Examples of suitable alkoxylated ethers include PPG-10 butyl ether, PPG-11 butyl ether, PPG-12 butyl ether, PPG-13 butyl ether, PPG-14 butyl ether, PPG-15 butyl ether, PPG-16 butyl ether, PPG-17 butyl ether, PPG-18 butyl ether, PPG-19 butyl ether, PPG-20 butyl ether, PPG-22 butyl ether, PPG-24 butyl ether, PPG-30 butyl ether, PPG-11 stearyl ether, PPG-15 stearyl ether, PPG-10 oleyl ether, PPG-7 lauryl ether, PPG-30 isocetyl ether, PPG-10 glyceryl ether, PPG-15 glyceryl ether, PPG-10 butyleneglycol ether, PPG-15 butylene glycol ether, PPG-27 glyceryl ether, PPG-30 cetyl ether, PPG-28 cetyl ether, PPG-10 cetyl ether, PPG-10 hexylene glycol ether, PPG-15 hexylene glycol ether, PPG-10 1,2,6-hexanetriol ether, PPG-15 1,2,6-hexanetriol ether, and mixtures thereof.

Examples of alkoxylated diethers include PPG-10 1,4-butanediol diether, PPG-12 1,4-butanediol diether, PPG-14 1,4-butanediol diether, PPG-2 butanediol diether, PPG-10 1,6-hexanediol diether, PPG-12 1,6-hexanediol diether, PPG-14 hexanediol diether, PPG-20 hexanediol diether, and mixtures thereof. Preferred are those selected from the group consisting of PPG-10 1,4-butanediol diether, PPG-12 1,4-butanediol diether, PPG-10 1,6-hexanediol diether, and PPG-12 hexanediol diether, and mixtures thereof.

Examples of suitable alkoxylated diesters and trimesters are disclosed in U.S. Pat. Nos. 5,382,377, 5,455,025 and 5,597,555, assigned to Croda Inc. and incorporated herein by reference.

Suitable lipids include $C_8$–$C_{20}$ alcohol monosorbitan esters, $C_8$–$C_{20}$ alcohol sorbitan diesters, $C_8$–$C_{20}$ alcohol sorbitan triesters, $C_8$–$C_{20}$ alcohol sucrose monoesters, $C_8$–$C_{20}$ alcohol sucrose diesters, $C_8$–$C_{20}$ alcohol sucrose triesters, and $C_8$–$C_{20}$ fatty alcohol esters of $C_2$–$C_{62}$-hydroxy acids. Examples of specific suitable lipids are sorbitan diisostearate, sorbitan dioleate, sorbitan distearate, sorbitan isosotearate, sorbitan laurate, sorbitan oleate, sorbitan palmitate, sorbitan sesquioleate, sorbitan esquistearte, sorbitan stearate, sorbitan triiostearte, sorbitan trioleate, orbitan tristeate, sucrose cocoate, sucrodilaurate, sucrose distearate, sucrose laurate, sucrose myristate, sucrose oleate, sucrose palmitate, sucrose ricinoleate, sucrose stearate, sucrose tribehenate, sucrose tristearate, myristyl lactate, stearyl lactate, isostearyl lactate, cetyl lactate, palmityl lactate, cocoyl lactate, and mixtures thereof.

Other suitable emollients include mineral oil, petrolatum, cholesterol, dimethicone, dimethiconol, stearyl alcohol, cetyl alcohol, behenyl alcohol, diisopropyl adipate, isopropyl myristate, myristyl myristate, cetyl ricinoleate, sorbitan distearte, sorbitan dilaurate, sorbitan stearate, sorbitan laurate, sucrose laurate, sucrose dilaurate, sodium isostearyl lactylate, lauryl pidolate, sorbitan stearate, stearyl acohol, cetyl alcohol, behenyl alcohol, PPG-14 butyl ether, PPG-15 stearyl ether, and mixtures thereof.

EMULSIFIERS

The compositions of the invention may also include various emulsifiers. In the final product compositions of the invention, emulsifiers may be included in the amount of up to about 10%, preferably, in the amount of from about 0.5% to about 5% by weight of the composition. The examples of suitable emulsifiers include stearamidopropyl PG-dimonium chloride phosphate, stearamidopropyl ethyldimonium ethosulfate, stearamidopropyl dimethyl(myristyl acetate) ammonium chloride, stearamidopropyl dimethyl cetearyl ammonium tosylate, stearamidopropyl dimethyl ammonium chloride, stearamidopropyl dimethyl ammonium lactate, polyethyleneglycols, polypropyleneglyocis, and mixtures thereof.

ANTI-DANDRUFF

The compositions of the invention may also include antidandruff agents. The examples of suitable antidandruff agents include zinc pyrithione, sulphur, and selenium sulfide.

HAIR OXIDIZERS

The compositions of the invention may also include hair oxidizing/reducing agents. The examples of suitable hair oxidizing/reducing agents include hydrogen peroxide, perborate, thioglycolates and persulfate salts.

THICKENERS

The compositions of the invention may also include various thickeners, such as cross-linked acrylates, nonionic polyacrylamides, xanthan gum, guar gum, gellan gum, and the like; polyalkyl siloxanes, polyaryl siloxanes, and aminosilicones. In the final product compositions of the invention, thickeners may be included in the amount of up to about 10%, preferably, in the amount of from about 0.2% to about 5% by weight of the composition.

The specific examples of the suitable thickening silicone compounds include polydimethylsiloxane, phenylsilicone, polydiethylsiloxane, and polymethylphenylsiloxane. Some of the suitable silicone compounds are described in European Patent Application EP 95,238 and U.S. Pat. No. 4,185,017, which are incorporated herein by reference. The compositions of the invention may also include silicone polymer materials, which provide both style retention and conditioning benefits to the hair. Such materials are described in U.S. Pat. No. 4,902,499, which is incorporated herein by reference.

HAIR CONDITIONING AGENTS

The compositions of the invention may also include hydrolyzed animal protein hair conditioning agents. Croda Incorporated sells an example of a commercially available material under the tradename Crotein Q-RTM. Other examples include urea, glycerol, and propoxylated glycerols, including those described in U.S. Pat. No. 4,976,953, which is incorporated by reference herein.

HAIR SETTING AGENTS

The compositions of the invention may also include a hair setting agent to impart styling benefits upon application to hair. The hair setting polymers may be homopolymers, copolymers, terpolymers, etc. For convenience in describing the polymers hereof, monomeric units present in the polymers may be referred to as the monomers from which they can be derived. The monomers can be ionic (e.g., anionic, cationic, amphoteric, zwitterionic) or nonionic.

Examples of anionic monomers include unsaturated carboxylic acid monomers such as acrylic acid, methacrylic acid, maleic acid, maleic acid half ester, itaconic acid, fumaric acid, and crotonic acid; half esters of an unsaturated polybasic acid anhydride such as succinic anhydride, phthalic anhydride or the like with a hydroxyl group-containing acrylate and/or methacrylate such as hydroxyethyl acrylate and, hydroxyethyl methacrylate, hydroxypropyl acrylate and the like; monomers having a sulfonic acid group such as styrenesulfonic acid, sulfoethyl acrylate and methacrylate, and the like; and monomers having a phosphoric acid group such as acid phosphooxyethyl acrylate and methacrylate, 3-chloro-2-acid phosphooxypropyl acrylate and methacrylate, and the like.

Examples of cationic monomers include monomers derived from acrylic acid or methacrylic acid, and a quaternarized epihalohydrin product of a trialkylamine having 1 to 5 carbon atoms in the alkyl such as (meth)acryloxypropyltrimethylammonium chloride and (meth)acryloxypropyl-triethylammonium bromide; amine derivatives of methacrylic acid or amine derivatives of methacrylamide derived from methacrylic acid or methacrylamide and a dialkylalkanolamine having $C_1$–$C_6$ alkyl groups such as dimethylaminoethyl(meth)acrylate, diethylaminoethyl(meth)acrylate, dimethylaminopropyl(meth)acrylate, or dimethylaminopropyl(meth)acrylamide.

Examples of the amphoteric monomers include zwitterionized derivatives of the aforementioned amine derivatives of (meth)acrylic acids or the amine derivatives of (meth)acrylamide such as dimethylaminoethyl(meth)acrylate, dimethylaminopropyl(meth)acrylamide by a halogenated fatty acid salt such as potassium monochloroacetate, sodium monobromopropionate, aminomethylpropanol salt of monochloroacetic acid, triethanolamine salts of monochloroacetic acid and the like; and amine derivatives of (meth)acrylic acid or (meth)acrylamide, as discussed above, modified with propanesultone.

Examples of nonionic monomers are acrylic or methacrylic acid esters of $C_1$–$C_{24}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, styrene; chlorostyrene; vinyl esters such as vinyl acetate; vinyl chloride; vinylidene chloride; acrylonitrile; alpha-methylstyrene; t-butylstyrene; butadiene; cyclohexadiene; ethylene; propylene; vinyl toluene; alkoxyalkyl (meth)acrylate, methoxy ethyl(meth)acrylate, butoxyethyl (meth)acrylate; allyl acrylate, allyl methacrylate, cyclohexyl acrylate and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol di-acrylate and -methacrylate, diacetonacrylamide, isobornyl(meth)acrylate, n-butyl methacrylate, isobutyl methacrylate, 2-ethylhexyl methacrylate, methyl methacrylate, t-butylacrylate, t-butylmethacrylate, and mixtures thereof.

Examples of anionic hair styling polymers are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride, acrylic copolymers and terpolymers containing acrylic acid or methacrylic acid.

Examples of cationic hair styling polymers are copolymers of amino-functional acrylate monomers such as lower alkylamino alkyl acrylate or methacrylate monomers such as dimethyl aminoethylmethacrylate with compatible monomers such as N-vinylpyrrolidone or alkyl methacrylates such as methyl methacrylate and ethyl methacrylate and alkyl acrylates such as methyl acrylate and butyl acrylate.

MISCELLANEOUS COMPONENTS

The compositions of the invention may also include a wide range of miscellaneous ingredients. Some suitable miscellaneous ingredients commonly used in the cosmetic and personal care industry are described in The CTFA Cosmetic Ingredient Handbook, (2nd Ed., 1992), which is incorporated by reference herein.

Thus, the compositions of the invention may also include one or more absorbents, anti-acne agents, antiperspirants, anti-caking agents, antifoaming agents, antimicrobial agents, antioxidants, antidandruff agents, astringents, binders, buffers, biological additives, buffering agents, bulking agents, chelating agents, chemical additives, coupling agents, conditioners, colorants, cosmetic astringents, cosmetic biocides, denaturants, drug astringents, detergents, dispersants, external analgesics, film formers, foaming agents, fragrance components, humectants, keratolytics, opacifying agents, pH adjusters, preservatives, propellants, proteins, retinoids, reducing agents, sequestrants, skin bleaching agents, skin-conditioning agents (humectants, miscellaneous, and occulsive), skin soothing agents, skin healing agents, softeners, solubilizing agents, lubricants, penetrants, plastisizers, solvents and co-solvents, sunscreening additives, salts, essential oils, and vitamins.

The examples of suitable pH adjusters include sodium hydroxide, triethanoleamine, and aminomethylpropanol, and mixtures thereof. If pH adjusters are present in a final product composition, the amount may vary from about 0.01% to about 5%, preferably, from about 0.1% to about 2% by weight of the composition.

The examples of suitable film formers include glycerin/diethylene glycol myrystate copolymer, glycerin/diethylene glycol adipate copolymer, ethyl ester of PVM/MA copolymer, PVP/dimethiconylacrylate/polycarbamyl/polyglycol ester, and mixtures thereof. If the film formers are present in the final product compositions, the amount may vary from about 0.1% to about 15.0% by weight of the composition, preferably, from about 0.1% to about 2.5% by weight of the composition.

The examples of suitable vitamins include tocopherol, tocopherol acetate, retinoic acid, retinol, and retinoids.

The examples of suitable anti-acne medicaments include resorcinol, sulfur, salicylic acid, erythromycin, zinc, and benzoyl peroxide.

The examples of suitable skin bleaching or lightening agents include hydroquinone, and kojic acid. The examples of suitable aesthetic components such as fragrances, pigments, colorings, and the like, include panthenol and derivatives (e.g., ethyl panthenol), aloe vera, pantothenic acid and its derivatives, clove oil, menthol, camphor, eucalyptus oil, eugenol, menthyl lactate, witch hazel distillate, allantoin, bisabolol, and dipotassium glycyrrhizinate.

The compositions of the invention are further illustrated in the examples that follow.

EXAMPLE 1

Preparation of 1-methyl-1-((erucylamido-)ethyl)-2-erucyl immidazolinium methyl sulfate 3132 g (4.62 moles) of erucic acid and 216 g (2.1 moles) of diethylenetriamine are placed in a dry stirred pressure vessel fitted with a nitrogen inlet. The vessel is purged with nitrogen and heated to 170° C. for 4–5 hours. The reaction mixture is then heated to 180° C. and vacuum is applied for another 4–5 hours. The reaction mixture is cooled to 95–100° C. and approximately 1.5 kg of cetearyl alcohol is added. The reaction mixture is further cooled to 75–80° C. and 250 g of dimethyl sulfate is slowly added with stirring. Once all dimethyl sulfate is added, the reaction mixture is held at 75–80° C. for approximately one hour, providing 1-methyl-1-((erucylamido-)ethyl)-2-erucyl immidazolinium methyl sulfate as the product.

EXAMPLE 2

Preparation of 1-methyl-1-(erucic rapeseed-)-ethyl)-2-(erucic rapeseed-)immidazolinium methyl sulfate (Mixture of dialkyl imidazoline Quats of Hydrogenated Rapeseed Oil)

1843.6 g (1.88 moles) of hydrogenated rapeseed oil and 283.34 g (2.75 moles) of diethylenetriamine were placed in a dry stirred pressure vessel fitted with a nitrogen inlet. The vessel was purged with nitrogen and heated to 165° C. for 5 hours until a base value of 76 was reached. The reaction mixture was then heated to 190° C. and vacuum was applied for 5 hours to obtain a 94% tertiary amine content. The resulting imidazoline intermediate was then cooled to 95° C. and 1772 g of cetearyl alcohol were added to act as solvent. The reaction mixture was further cooled to 85° C. and 330 g (2.6 moles) of dimethyl sulfate were slowly added over a 30-minute period with stirring. Once all dimethyl sulfate was added, the reaction mixture was held at 85–90° C. for another 60 minutes. The resulting light yellow solid product included di-hydrogenated rapeseed oil imidazoline quat and cetearyl alcohol. The cationic activity of the mixture was 54%. The product was capable of being flaked or pastilled.

EXAMPLE 3

Preparation of 1-methyl-1-N-(n-propyl)-2-erucyl immidazolinium methyl sulfate

| Component | Ingredient | % of total cationic activity | Total cationic activity |
|---|---|---|---|
| Component (a) | Mixture of Table 1 | 70% | 45% |
| Component (b) | Compound (XXIII) | 30% | |
| Solvent | Mixture of cetearyl alcohol (80%) and 1,3-butanediol (20%) | — | |

EXAMPLE 5

Quat Raw Material 2

Quat Raw Material 2 has the following composition:

| Component | Ingredient | % of total cationic activity | Total cationic activity |
|---|---|---|---|
| Component (a) | di-behenyl immidazolinium methasulfate | 60% | 25% |
| Component (b) | Cetrimonium methosylfate | 40% | |
| Solvent | Cetyl alcohol | — | |

EXAMPLE 6

Quat Raw Material 3

Quat Raw Material 2 has the following composition:

| Component | Ingredient | % of total cationic activity | Total cationic activity |
|---|---|---|---|
| Component (a) | di-behenyl immidazolinium methasulfate | 70% | 25% |
| Component (b) | Cetrimonium methosylfate | 3% | |
| Solvent | Cetyl alcohol | — | |

EXAMPLE 7

Quat Raw Material 4

Quat Raw Material 2 has the following composition:

| Component | Ingredient | % of total cationic activity | Total cationic activity |
|---|---|---|---|
| Component (a) | Mixture of Table 1 | 60% | 25% |
| Component (b) | Lauryl trimethyl ammonium | 40% | |

| Component | Ingredient | % of total cationic activity | Total cationic activity |
|---|---|---|---|
| Solvent | chloride<br>Cetyl alcohol | — | |

EXAMPLE 8
Sunscreen Lotion

A sunscreen lotion includes the following ingredients:

| Phase A | |
|---|---|
| Ingredient(s) | % W/W |
| Di-erucic imidazoline quat | 1.0 |
| Behentrimonuim Chloride | 1.0 |
| Benzophenone 3 | 5.0 |
| Cetearyl Alcohol | 4.0 |
| Crodamol OS (Octyl Stearate) | 15.0 |
| Octyl Methoxycinnamate | 7.5 |

| Phase B | |
|---|---|
| Ingredient | W/W % |
| Water | 65.50 |

| Phase C | |
|---|---|
| Ingredient | W/W % |
| Germaben II (preservative) | 1.0 |

The ingredients of Phase A are combined and heated to 75° C. In a separate vessel, the ingredients of Phase B are also combined and heated to 75° C. Phase A is added to Phase B with stirring, and the stirring is continued while the combined phases are cooled to 40° C. Phase C is added, the cooling is continued to 25° C., providing the desired lotion.

EXAMPLE 9
Sunscreen Spray Lotion

A sunscreen spray lotion includes the following ingredients:

| Phase A | |
|---|---|
| Ingredient | % W/W |
| Di-erucic imidazoline quat | 1.0 |
| Cetrimonium Chloride | 1.0 |
| PPG-3 Benzyl Myristate | 10.0 |
| Benzophenone 3 | 6.0 |
| Octyl Methoxycinnamate | 7.0 |
| Menthyl Anthranilate | 5.0 |
| Cromollient SCE<br>(Di-PPG-2 Myreth-10 Adipate) | 3.0 |

| Phase B | |
|---|---|
| Ingredient | W/W % |
| Water | 66 |
| Sodium Hydroxide | 0.1 |

| Phase C | |
|---|---|
| Ingredient | W/W % |
| Germaben II (preservative) | 1.0 |

The ingredients of Phase A are combined and heated to 75° C. In a separate vessel, the ingredients of Phase B are also combined and heated to 75° C. Phase A is added to Phase B with stirring, and the stirring is continued while the combined phases are cooled to 40° C. Phase C is added, the cooling is continued to 25° C., providing the desired lotion.

EXAMPLE 11

Hair Conditioner

| Phase A | |
|---|---|
| Ingredient | % W/W |
| Di-C20–24 Imidazoline Quat | 1.0 |
| Cetrimonium Chloride | 1.0 |
| Cromollient SCE (Di-PPG-2 Myreth-10 Adipate) | 4.0 |
| Cetyl Alcohol | 4.0 |

| Phase B | |
|---|---|
| Ingredient | W/W % |
| Water | 89 |

| Phase C | |
|---|---|
| Ingredient | W/W % |
| Germaben II (preservative) | 1.0 |

The ingredients of Phase A are combined and heated to 75° C. In a separate vessel, the ingredients of Phase B are also combined and heated to 75° C. Phase A is added to Phase B with stirring, and the stirring is continued while the combined phases are cooled to 40° C. Phase C is added, the cooling is continued to 25° C., providing the desired lotion.

EXAMPLE 12

Conditioning Shampoo

A hair conditioner includes the following ingredients:

Phase A

| Ingredient | % W/W |
|---|---|
| Ammonium Lauryl Sulfate | 25.0 |
| Ammonium Laureth Sulfate | 12.0 |
| Crosultaine C-50 (Cocamidopropyl Hydroxysultaine) | 3.0 |
| Lauramide DEA | 1.0 |
| Cromollient SCE (Di-PPG-2 Myreth-10 Adipate) | 4.0 |
| Germaben II (Preservative) | 1.0 |

Phase B

| Ingredient | W/W % |
|---|---|
| Di-Erucic Imidazoline Quat | 2.0 |

The ingredients of phase A are combined and heated to 60° C. Phase B is added to the combined phase A and with continued stirring while allowing the mixture to cool to 25° C.

EXAMPLE 13

Soft & Shine Conditioner

A soft and shine conditioner includes the following ingredients.

Phase A

| Ingredient | % W/W |
|---|---|
| Water | 86.26 |
| Mixture of Di-behenyl imidazolinium Methosulfate and Cetrimonium Methasulfate (7/3 w/w) in Cetearyl alcohol (70% actives) | 2.14 |
| CRODACOL C-70 (Cetyl Alcohol) | 1.00 |
| CRODACOL S-70 (Stearyl Alcohol) | 3.00 |
| CRILLET 3 (Polysorbate 60) | 1.00 |

Part B

| Ingredient | W/W % |
|---|---|
| INCROMINE SB (Stearamidopropyl Dimethylamine) | 0.5 |
| Cyclopentasiloxane (and) Dimethicone (1) | 4.0 |
| Dimethicone (2) | 0.5 |
| Disodium EDTA | 0.2 |
| Propylene Glycol (and) Diazolidinyl Urea (and) Methylparaben (and) Propylparaben (3) | 1.00 |
| Citric acid | 0.4 |

Part C

| Ingredient | W/W % |
|---|---|
| Germaben II (Preservative) | 1.0 |

EXAMPLE 14

Vitamin E-containing Conditioner

The vitamin E-containing conditioner has the following ingredients.

Phase A

| Ingredient | % W/W |
|---|---|
| Deionized Water | 92.50 |
| CRODACOL S-70 (Stearyl Alcohol) | 3.80 |
| Mixture of Di-behenyl imidazolinium Methosulfate and Cetrimonium Methasulfate (7/3 w/w) in Cetearyl alcohol (70% actives) | 2.20 |

Part B

| Ingredient | W/W % |
|---|---|
| DL-α Tocopherol Acetate (1) | 0.50 |

Part C

| Ingredient | W/W % |
|---|---|
| Propylene Glycol (and) Diazolidinyl Urea (and) Methylparaben (and) Propylparaben (2) | 1.00 |

| | Deposition of Vitamin E (mg of Vit E/100 g of hair) | |
|---|---|---|
| Ingredient | Virgin Hair | Bleached hair |
| Behentrimonium Chloride | 86.3 | 57.6 |
| Mixture of Di-behenyl imidazolinium Methosulfate and Cetrimonium Methasulfate (7/3 w/w) | 180 | 80.9 |

EXAMPLE 16

Deposition of Vitamin E (Comparative Experiment 2)

Test conditioning shampoo formulations A and B were prepared using a mixture of Di-behenyl imidazolinium Methosulfate and Cetrimonium Methasulfate in 7/3 w/w ratio of quats to one another as the active conditioning ingredient. The added conditioning ingredient, which is generally derived from HEAR oil, contained 70% active quats by cationic activity in cetearyl alcohol. Test formulation A contained 1% of quat by cationic activity and test formulation A contained 0.5% of quat by cationic activity. Polyquaternium-10, a well-known polymeric conditioner, was used in the reference formulation C. The smaller amount of Polyquaternium-10 was used to reflect the cost benefit consideration.

Hair samples were treated with the respective conditioning shampoo for 3 minutes and rinsed off under 40° C. running tap water with a flow rate of 2.5 l/min for 20 seconds. The total substantivity was determined by two consecutive extractions by PVCS Method #7-1. Only trace of Vitamin E was detected in the third extraction solution.

The determined total substantivity of Vitamin E delivered from these conditioning shampoo samples is presented below:

| Ingredient//Amount added to the Test Shampoo | Average Substantivity (mg Vit E/100 g hair) by PVCS Method # 7-1 | | |
|---|---|---|---|
| | First extraction | Second extraction | Total |
| Mixture of Di-behenyl imidazolinium Methosulfate and Cetrimonium Methasulfate (7/3 w/w)// 1% cationic activity | 52.7 | 23.1 | 75.8 |
| Mixture of di-behenyl imidazolinium methosulfate and cetrimonium methasulfate (7/3 w/w ratio) in cetearyl alcohol (70% actives)// 0.5% cationic activity | 46.4 | 44.6 | 91.0 |
| Polyquaternium-10// 0.3% by cationic activity | 24.3 | 15.6 | 39.9 |

The conditioning shampoo samples containing di-behenyl imidazolinium methosulfate showed better deposition of Vitamin E onto hair surface than the sample containing Polyquaternium-10. Also, the deposition of Vitamin E on hair surface was enhanced by an increase in the concentration of di-behenyl imidazolinium methosulfate in the formulation

EXAMPLE 17

Emulfication/Performance Comparison: Stability

Cetrimonium Methosulfate, Dibehenyl Imidazolinium Methosulfate, and a mixture of Dibehenyl Imidazolinium methosulfate+Cetrimonium Methosulfate+Cetearyl alcohol were used to evaluate emulsification vs. performance of quat mixtures.

Lotions were prepared as shown below:

| Ingredient | AP-1 (%) | AP-2 (%) | AP-3 (%) |
|---|---|---|---|
| Cetrimonium quat | 1.5 | 0 | 0 |
| Dibehenyl Imidazolinium quat | 0 | 1.5 | 0 |
| 40:60 mix of Cetrimonium:Dibehenyl Imidazolinium | 0 | 0 | 1.5 |
| Crodacol S-70 | 4.5 | 4.5 | 4.5 |
| Deionized Water | 94 | 94 | 94 |

Stability of each lotion at 24 hours was evaluated. Lotion AP-1 (Cetrimonium Methosulfate alone) was stable. Lotion AP-2 (Dibehenyl Imidazolinium alone) was unstable. Lotion AP-3 (60:40 mixture of Cetrimonium methosulfate and Dibehenyl Imidazolinium) was stable.

EXAMPLE 18

Emulfication/Performance Comparison (Performance)

Only stable lotions were evaluated for performance.

Evaluation procedure was as follows. Virgin (V) and Bleached (B) hair tresses weighing about 3–4 g each were washed with a standard shampoo base and allowed to dry overnight. The tresses where then treated with Lotions AP1 and AP-3 and allowed to dry in a constant temperature and humidity chamber at 25° C. and 50% relative humidity. Combing force was measured using a Dia-Stron Miniature Tensile Tester. Total Work measures the force necessary to pass a comb through a hair tress and basically is a measurement of the Overall Combing properties of the hair. Peak Load is the highest force seen during combing and is indicative of how well a product detangles hair during combing.

The results were as follows:

| | AP-1 (%) | AP-3 (%) |
|---|---|---|
| Peak Load (B) | 54.4 | 70.7 |
| Total load (B) | 25.5 | 38.1 |
| Peak Load (V) | 46.3 | 58.7 |
| Total load (V) | 15.5 | 20.7 |

The data show that combinations of Dibehenyl Imidazolinium methosulfate and Cetrimonium Methosulfate produce stable lotions that have improved hair-conditioning properties over just Cetrimonium Methosulfate lotions.

The results show that Lotion AP-3 was better at reducing Peak Load forces and Total Work on both bleached and virgin hair compared to Lotion AP-1.

Unless stated to the contrary, any use of the words such as "including," "containing," "comprising," "having" and the like, means "including without limitation" and shall not be construed to limit any general statement that it follows to the specific or similar items or matters immediately following it.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A hair and skin conditioning formulation comprising:

(a) at least one dialkyl quat and at least one monoalkyl quat, wherein either
said at least one monoalkyl quat is a mixture of monoalkyl imidazoline quats, or
said at least one dialkyl quat is a mixture of dialkyl imidazoline quats;

(b) a solvent; and (c) at least one ingredient chosen from a surfactant, fatty amine, amidoamine, sunscreen compounds, emollient, emulsifier, hair oxidizer, thickeners, hair conditioning agent, hair setting agent, absorbent, antifoaming agent, antimicrobial agent, antioxidant, antiseptic agent, astringent, binder, buffer, biological additive, botanical extracts, buffering agent, bulking agent, chelating agent, chemical additive, coupling agent, conditioner, colorant, cosmetic astringent, cosmetic biocide, dispersant, film former, foaming agent, fragrance component, humectant, hydrophobic ingredient, keratolytic, moisturizer, opacifying agent, pH adjuster, preservative, protein, retinoid, reducing agent, sequestrant, softener, solubilizing agent, lubricant, penetrant, plastisizer, solvent and co-solvent, sunscreen additive, salt, silicone, essential oil, vitamin, wax, or mixtures thereof, said formulation being a conditioner.

2. The conditioning formulation of claim 1, wherein said solvent is selected from a group consisting of fatty alcohol, isopropyl alcohol, SDA-40, glycol and mixtures thereof.

3. The conditioning formulation of claim 1, further comprising at least one amidoamine.

4. The conditioning formulation of claim 1, wherein said dialkyl imidazoline quat is derived from HEAR oil and said monoalkyl quat is cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, stearamidopropyl PG-dimonium chloride phosphate, stearamidopropyl ethyldimonium ethosulfate, stearamidopropyl dimethyl(myristyl acetate)ammonium chloride, stearamidopropyl dimethyl cetearyl ammonium tosylate, stearamidopropyl dimethyl ammonium chloride, stearamidopropyl and dimethyl ammonium lactate.

5. The conditioning formulation of claim 4, wherein said HEAR oil is a hydrogenated HEAR oil.

6. The conditioning formulation of claim 1, wherein said mixture of dialkyl imidazoline quats includes at least one dialkyl imidazoline quat having at least one alkyl group having from 16 to 30 carbon atoms.

7. The conditioning formulation of claim 1, wherein said at least one monoalkyl quat includes at least one alkyl group having from 16 to 30 carbon atoms.

8. The conditioning formulation of claim 1, wherein said at least one dialkyl quat is a dialkyl imidazoline quats of the formula (I):

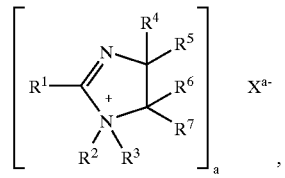

where X is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

a is the ionic charge of X;

$R^1$, $R^2$, and $R^3$ are independently hydrogen, $C_1$–$C_{30}$ alkyl, $C_1$–$C_{30}$ alkylhydroxy, $C_1$–$C_{30}$ alkyl amido $R_{(C1-C6)}$, $C_1$–$C_{30}$ alkylaryl amido $R_{(C1-C6)}$ or $C_1$–$C_{30}$ alkylhydroxy amido $R_{(C1-C6)}$, $R_{(C1-C6)}$ being $C_1$–$C_6$ alkylene or benzyl;

two of $R^1$, $R^2$, and $R^3$ are independently $C_{10}$–$C_{30}$ alkyl, $C_{10}$–$C_{30}$ alkylhydroxy, $C_{10}$–$C_{30}$ alkyl amido $R_{(C1-C6)}$, $C_{10}$–$C_{30}$ alkylaryl amido $R_{(C1-C6)}$ or $C_{10}$–$C_{30}$ alkylhydroxy amido $R_{(C1-C6)}$;

the remaining one of $R^1$, $R^2$ and $R^3$ is hydrogen, $C_1$–$C_8$ alkyl, $C_1$–$C_8$ alkylhydroxy, $C_1$–$C_8$ alkyl amido $R_{(C1-C6)}$, $C_1$–$C_8$ alkylaryl amido $R_{(C1-C6)}$ or $C_1$–$C_8$ alkylhydroxy amido $R_{(C1-C6)}$;

$R^4$, $R^5$, $R^6$, and $R^7$, same or different, are independently hydrogen, alkyl, arylalkyl, alkylaryl, fluoro, bromo, chloro, iodo, acetoxy, alkylacetoxy, arylacetoxy, carboxy, alkylcarboxy, hydroxy or alkoxyhydroxy.

9. The conditioning formulation of claim 1, wherein said at least one dialkyl quat is a dialkyl imidazoline quat of the formula (II):

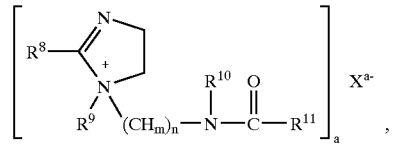

wherein X is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

a is the ionic charge of X;

n varies from 1 to 3;

m is 1 or 2;

$R^8$ and $R^{11}$, same or different, are independently $C_{16}$–$C_{30}$ alkyl or $C_{16}$–$C_{30}$ alkylhydroxy;

$R^9$ is hydrogen or $C_1$–$C_3$ alkyl; and $R^{10}$ is hydrogen, alkyl, arylalkyl, alkylaryl, fluoro, bromo, chloro, iodo, acetoxy, alkylacetoxy, arylacetoxy, carboxy, alkylcarboxy, hydroxy or alkoxyhydroxy.

10. The conditioning formulation of claim 1, wherein said at least one said monoalkyl quat has the structure

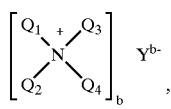

wherein Y is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

b is the ionic charge of Y;

$Q_1$ is selected from the group consisting of $C_{12}$–$C_{22}$ alkyl, $C_{12}$–$C_{22}$ alkyl amido $C_1$–$C_6$ alkylene, and $C_{12}$–$C_{22}$ alkylhydroxy; and $Q_2$, $Q_3$ and $Q_4$ are independently $C_1$–$C_6$ alkyl or benzyl.

11. The conditioning formulation of claim 1, wherein said at least one monoalkyl quat is a monoalkyl imidazoline quat of the formula (IV):

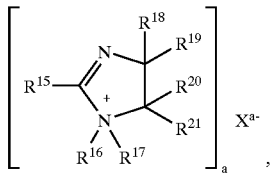

wherein X is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

a is the ionic charge of X;

$R^{15}$, $R^{16}$ and $R^{17}$ are independently hydrogen, $C_1$–$C_{30}$ alkyl, $C_1$–$C_{30}$ alkylhydroxy, $C_1$–$C_{30}$ alkyl amido $R_{(C1-C6)}$, $C_1$–$C_{30}$ alkylaryl amido $R_{(C1-C6)}$, or $C_1$–$C_{30}$ alkylhydroxy amido $R_{(C1-C6)}$, wherein $R_{(C1-C6)}$ is a $C_1$–$C_6$ alkylene or benzyl;

one of $R^{15}$, $R^{16}$ and $R^{17}$ is $C_1$–$C_{30}$ alkyl, $C_{10}$–$C_{30}$ alkylhydroxy, $C_{10}$–$C_{30}$ alkyl amido $R_{(C1-C6)}$, $C_{10}$–$C_{30}$ alkylaryl amido $R_{(C1-C6)}$ or $C_{10}$–$C_{30}$ alkylhydroxy amido $R_{(C1-C6)}$;

the remaining two of $R^{15}$, $R^{16}$ and $R^{17}$ are independently hydrogen, $C_1$–$C_8$ alkyl, $C_1$–$C_8$ alkylhydroxy, $C_1$–$C_8$ alkyl amido $R_{(C1-C6)}$, $C_1$–$C_8$ alkylaryl amido $R_{(C1-C6)}$, or $C_1$–$C_8$ alkylhydroxy amido $R_{(C1-C6)}$;

$R^{18}$, $R^{19}$, $R^{20}$, and $R^{21}$, same or different, are independently selected from the group consisting of hydrogen, alkyl, arylalkyl, alkylaryl, fluoro, iodo, bromo and chloro, acetoxy, alkylacetoxy, arylacetoxy, carboxy, alkylcarboxy, hydroxy, and alkoxyhydroxy.

12. A shampoo formulation comprising:

(a) at least one dialkyl quat and at least one monoalkyl quat, wherein either
said at least one monoalkyl quat is a mixture of monoalkyl imidazoline quats, or
said at least one dialkyl quat is a mixture of dialkyl imidazoline quats;

(b) a solvent; and (c) at least one ingredient chosen from a surfactant, fatty amine, amidoamine, sunscreen compounds, emollient, emulsifier, anti-dandruff agent, hair oxidizer, thickeners, hair conditioning agent, absorbent, antiperspirant, anti-caking agent, antimicrobial agent, antioxidant, antiseptic agent, astringent, binder, buffer, biological additive, botanical extracts, buffering agent, bulking agent, chelating agent, chemical additive, coupling agent, conditioner, colorant, cosmetic biocide, denaturant, detergent, dispersant, film former, foaming agent, fragrance component, humectant, hydrophobic ingredient, keratolytic, moisturizer, opacifying agent, pH adjuster, preservative, protein, retinoid, reducing agent, sequestrant, skin bleaching agent, softener, solubilizing agent, lubricant, penetrant, plastisizer, solvent and co-solvent, sunscreen additive, salt, silicone, essential oil, vitamin, wax, or mixtures thereof, said formulation being a shampoo.

13. The shampoo formulation of claim 12, wherein said solvent is selected from a group consisting of fatty alcohol, isopropyl alcohol, SDA-40, glycol and mixtures thereof.

14. The shampoo formulation of claim 12, further comprising at least one amidoamine.

15. The shampoo formulation of claim 12, wherein said dialkyl imidazoline quat is derived from HEAR oil and said monoalkyl quat is cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, stearamidopropyl PG-dimonium chloride phosphate, stearamidopropyl ethyldimonium ethosulfate, stearamidopropyl dimethyl(myristyl acetate)ammonium chloride, stearamidopropyl dimethyl cetearyl ammonium tosylate, stearamidopropyl dimethyl ammonium chloride, stearamidopropyl and dimethyl ammonium lactate.

16. The shampoo formulation of claim 15, wherein said HEAR oil is a hydrogenated HEAR oil.

17. The shampoo formulation of claim 12, wherein said mixture of dialkyl imidazoline quats includes at least one dialkyl imidazoline quat having at least one alkyl group having from 16 to 30 carbon atoms.

18. The shampoo formulation of claim 12, wherein said at least one monoalkyl quat includes at least one alkyl group having from 16 to 30 carbon atoms.

19. The shampoo of claim 12, wherein said at least one dialkyl quat is a dialkyl imidazoline quat of the formula (I):

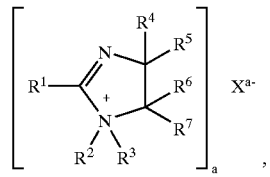

where X is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

a is the ionic charge of X;

$R^1$, $R^2$, and $R^3$ are independently hydrogen, $C_1$–$C_{30}$ alkyl, $C_1$–$C_{30}$ alkylhydroxy, $C_1$–$C_{30}$ alkyl amido $R_{(C1-C6)}$, $C_1$–$C_{30}$ alkylaryl amido $R_{(C1-C6)}$ or $C_1$–$C_{30}$ alkylhydroxy amido $R_{(C1-C6)}$, $R_{(C1-C6)}$ being $C_1$–$C_6$ alkylene or benzyl;

two of $R^1$, $R^2$, and $R^3$ are independently $C_{10}$–$C_{30}$ alkyl, $C_{10}$–$C_{30}$ alkylhydroxy, $C_{10}$–$C_{30}$ alkyl amido $R_{(C1-C6)}$, $C_{10}$–$C_{30}$ alkylaryl amido $R_{(C1-C6)}$ or $C_{10}$–$C_{30}$ alkylhydroxy amido $R_{(C1-C6)}$;

the remaining one of $R^1$, $R^2$ and $R^3$ is hydrogen, $C_1$–$C_8$ alkyl, $C_1$–$C_8$ alkylhydroxy, $C_1$–$C_8$ alkyl amido $R_{(C1-C6)}$, $C_1$–$C_8$ alkylaryl amido $R_{(C1-C6)}$ or $C_1$–$C_8$ alkylhydroxy amido $R_{(C1-C6)}$;

$R^4$, $R^5$, $R^6$, and $R^7$, same or different, are independently hydrogen, alkyl, arylalkyl, alkylaryl, fluoro, bromo, chloro, iodo, acetoxy, alkylacetoxy, arylacetoxy, carboxy, alkylcarboxy, hydroxy or alkoxyhydroxy.

20. The shampoo formulation of claim 12, wherein said at least one dialkyl quat is a dialkyl imidazoline quat of the formula (II):

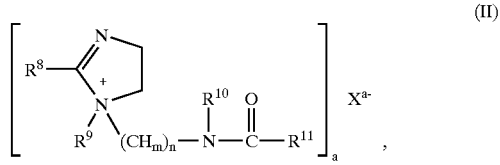

(II)

wherein X is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

a is the ionic charge of X;

n varies from 1 to 3;

m is 1 or 2;

$R^8$ and $R^{11}$, same or different, are independently $C_{16}$–$C_{30}$ alkyl or $C_{16}$–$C_{30}$ alkylhydroxy;

$R^9$ is hydrogen or $C_1$–$C_3$ alkyl; and $R^{10}$ is hydrogen, alkyl, arylalkyl, alkylaryl, fluoro, bromo, chloro, iodo, acetoxy, alkylacetoxy, arylacetoxy, carboxy, alkylcarboxy, hydroxy or alkoxyhydroxy.

21. The shampoo formulation of claim 12, wherein said at least one said monoalkyl quat has the structure

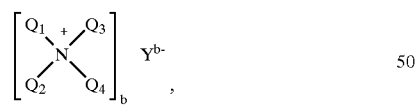

wherein Y is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

b is the ionic charge of Y;

$Q_1$ is selected from the group consisting of $C_{12}$–$C_{22}$ alkyl, $C_{12}$–$C_{22}$ alkyl amido $C_1$–$C_6$ alkylene, and $C_{12}$–$C_{22}$ alkylhydroxy; and $Q_2$, $Q_3$ and $Q_4$ are independently $C_1$–$C_6$ alkyl or benzyl.

22. The shampoo formulation of claim 12, wherein said at least one monoalkyl quat is a monoalkyl imidazoline quat of the formula (IV):

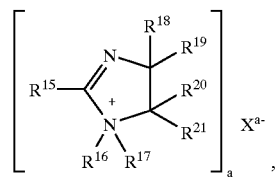

(IV)

wherein X is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

a is the ionic charge of X;

$R^{15}$, $R^{16}$ and $R^{17}$ are independently hydrogen, $C_1$–$C_{30}$ alkyl, $C_1$–$C_{30}$ alkylhydroxy, $C_1$–$C_{30}$ alkyl amido $R_{(C1-C6)}$, $C_1$–$C_{30}$ alkylaryl amido $R_{(C1-C6)}$, or $C_1$–$C_{30}$ alkylhydroxy amido $R_{(C1-C6)}$, wherein $R_{(C1-C6)}$ is a $C_1$–$C_6$ alkylene or benzyl;

one of $R^{15}$, $R^{16}$ and $R^{17}$ is $C_1$–$C_{30}$ alkyl, $C_{10}$–$C_{30}$ alkylhydroxy, $C_{10}$–$C_{30}$ alkyl amido $R_{(C1-C6)}$, $C_{10}$–$C_{30}$ alkylaryl amido $R_{(C1-C6)}$ or $C_{10}$–$C_{30}$ alkylhydroxy amido $R_{(C1-C6)}$;

the remaining two of $R^{15}$, $R^{16}$ and $R^{17}$ are independently hydrogen, $C_1$–$C_8$ alkyl, $C_1$–$C_8$ alkylhydroxy, $C_1$–$C_8$ alkyl amido $R_{(C1-C6)}$, $C_1$–$C_8$ alkylaryl amido $R_{(C1-C6)}$, or $C_1$–$C_8$ alkylhydroxy amido $R_{(C1-C6)}$;

$R^{18}$, $R^{19}$, $R^{20}$, and $R^{21}$, same or different, are independently selected from the group consisting of hydrogen, alkyl, arylalkyl, alkylaryl, fluoro, iodo, bromo and chloro, acetoxy, alkylacetoxy, arylacetoxy, carboxy, alkylcarboxy, hydroxy, and alkoxyhydroxy.

23. A hair detangling formulation comprising:
(a) at least one dialkyl quat and at least one monoalkyl quat, wherein either
said at least one monoalkyl quat is a mixture of monoalkyl imidazoline quats, or
said at least one dialkyl quat is a mixture of dialkyl imidazoline quats;
(b) a solvent; and
(c) at least one ingredient chosen from a surfactant, fatty amine, amidoamine, sunscreen compounds, emollient, emulsifier, thickeners, hair conditioning agent, absorbent, anti-caking agent, antifoaming agent, antimicrobial agent, antioxidant, antiseptic agent, astringent, binder, buffer, biological additive, botanical extracts, buffering agent, bulking agent, chelating agent, chemical additive, coupling agent, conditioner, colorant, cosmetic astringent, cosmetic biocide, denaturant, detergent, dispersant, film former, foaming agent, fragrance component, humectant, hydrophobic ingredient, keratolytic, moisturizer, opacifying agent, pH adjuster, preservative, propellant, protein, retinoid, reducing agent, sequestrant, softener, solubilizing agent, lubricant, penetrant, plastisizer, solvent and co-solvent, sunscreen additive, salt, silicone, essential oil, vitamin, wax, or mixtures thereof, said formulation being a hair detangler.

24. The hair detangling formulation of claim 23, wherein said solvent is selected from a group consisting of fatty alcohol, isopropyl alcohol, SDA-40, glycol and mixtures thereof.

25. The hair detangling formulation of claim 23, further comprising at least one amidoamine.

26. The hair detangling formulation of claim 23, wherein said dialkyl imidazoline quat is derived from HEAR oil and said monoalkyl quat is cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, stearamidopropyl PG-dimonium chloride phosphate, stearamidopropyl ethyldimonium ethosulfate, stearamidopropyl dimethyl(myristyl acetate)ammonium chloride, stearamidopropyl dimethyl cetearyl ammonium tosylate, stearamidopropyl dimethyl ammonium chloride, stearamidopropyl and dimethyl ammonium lactate.

27. The hair detangling formulation of claim 26, wherein said HEAR oil is a hydrogenated HEAR oil.

28. The hair detangling formulation of claim 23, wherein said mixture of dialkyl imidazoline quats includes at least one dialkyl imidazoline quat having at least one alkyl group having from 16 to 30 carbon atoms.

29. The hair detangling formulation of claim 23, wherein said at least one monoalkyl quat includes at least one alkyl group having from 16 to 30 carbon atoms.

30. The hair detangling formulation of claim 23, wherein said at least one dialkyl is a dialkyl imidazoline quat of the formula (I):

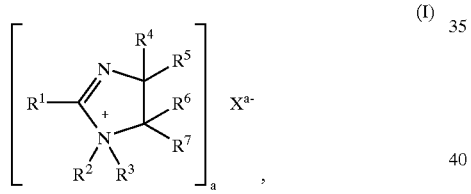

where X is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

a is the ionic charge of X;

$R^1$, $R^2$, and $R^3$ are independently hydrogen, $C_1$–$C_{30}$ alkyl, $C_1$–$C_{30}$ alkylhydroxy, $C_1$–$C_{30}$ alkyl amido $R_{(C1-C6)}$, $C_1$–$C_{30}$ alkylaryl amido $R_{(C1-C6)}$ or $C_1$–$C_{30}$ alkylhydroxy amido $R_{(C1-C6)}$, $R_{(C1-C6)}$ being $C_1$–$C_6$ alkylene or benzyl;

two of $R^1$, $R^2$, and $R^3$ are independently $C_{10}$–$C_{30}$ alkyl, $C_{10}$–$C_{30}$ alkylhydroxy, $C_{10}$–$C_{30}$ alkyl amido $R_{(C1-C6)}$, $C_{10}$–$C_{30}$ alkylaryl amido $R_{(C1-C6)}$ or $C_{10}$–$C_{30}$ alkylhydroxy amido $R_{(C1-C6)}$;

the remaining one of $R^1$, $R^2$ and $R^3$ is hydrogen, $C_1$–$C_8$ alkyl, $C_1$–$C_8$ alkylhydroxy, $C_1$–$C_8$ alkyl amido $R_{(C1-C6)}$, $C_1$–$C_8$ alkylaryl amido $R_{(C1-C6)}$ or $C_1$–$C_8$ alkylhydroxy amido $R_{(C1-C6)}$;

$R^4$, $R^5$, $R^6$, and $R^7$, same or different, are independently hydrogen, alkyl, arylalkyl, alkylaryl, fluoro, bromo, chloro, iodo, acetoxy, alkylacetoxy, arylacetoxy, carboxy, alkylcarboxy, hydroxy or alkoxyhydroxy.

31. The hair detangling formulation of claim 23, wherein said at least one dialkyl quat is a dialkyl imidazoline quat of the formula (II):

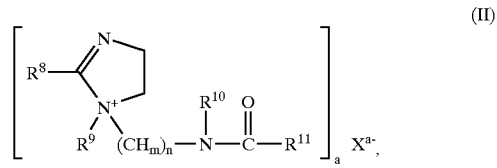

wherein X is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

a is the ionic charge of X;

n varies from 1 to 3;

m is 1 or 2;

$R^8$ and $R^{11}$, same or different, are independently $C_{16}$–$C_{30}$ alkyl or $C_{16}$–$C_{30}$ alkylhydroxy;

$R^9$ is hydrogen or $C_1$–$C_3$ alkyl; and $R^{10}$ is hydrogen, alkyl, arylalkyl, alkylaryl, fluoro, bromo, chloro, iodo, acetoxy, alkylacetoxy, arylacetoxy, carboxy, alkylcarboxy, hydroxy or alkoxyhydroxy.

32. The hair detangling formulation of claim 23, wherein said at least one said monoalkyl quat has the structure

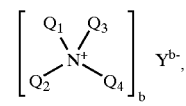

wherein Y is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

b is the ionic charge of Y;

$Q_1$ is selected from the group consisting of $C_{12}$–$C_{22}$ alkyl, $C_{12}$–$C_{22}$ alkyl amido $C_1$–$C_6$ alkylene, and $C_{12}$–$C_{22}$ alkylhydroxy; and $Q_2$, $Q_3$ and $Q_4$ are independently $C_1$–$C_6$ alkyl or benzyl.

33. The hair detangling formulation of claim 23, wherein said at least one monoalkyl quat is a monoalkyl imidazoline quat of the formula (IV):

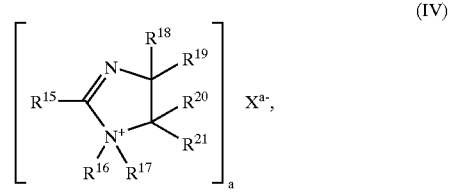

wherein X is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

a is the ionic charge of X;

$R^{15}$, $R^{16}$ and $R^{17}$ are independently hydrogen, $C_1$–$C_{30}$ alkyl, $C_1$–$C_{30}$ alkylhydroxy, $C_1$–$C_{30}$ alkyl amido $R_{(C1-C6)}$, $C_1$–$C_{30}$ alkylaryl amido $R_{(C1-C6)}$, or $C_1$–$C_{30}$ alkylhydroxy amido $R_{(C1-C6)}$, wherein $R_{(C1-C6)}$ is a $C_1$–$C_6$ alkylene or benzyl;

one of $R^{15}$, $R^{16}$ and $R^{17}$ is $C_1$–$C_{30}$ alkyl, $C_{10}$–$C_{30}$ alkylhydroxy, $C_{10}$–$C_{30}$ alkyl amido $R_{(C1-C6)}$, $C_{10}$–$C_{30}$ alkylaryl amido $R_{(C1-C6)}$ or $C_{10}$–$C_{30}$ alkylhydroxy amido $R_{(C1-C6)}$;

the remaining two of $R^{15}$, $R^{16}$ and $R^{17}$ are independently hydrogen, $C_1$–$C_8$ alkyl, $C_1$–$C_8$ alkylhydroxy, $C_1$–$C_8$ alkyl amido $R_{(C1-C6)}$, $C_1$–$C_8$ alkylaryl amido $R_{(C1-C6)}$, or $C_1$–$C_8$ alkylhydroxy amido $R_{(C1-C6)}$;

$R^{18}$, $R^{19}$, $R^{20}$, and $R^{21}$, same or different, are independently selected from the group consisting of hydrogen, alkyl, arylalkyl, alkylaryl, fluoro, iodo, bromo and chloro, acetoxy, alkylacetoxy, arylacetoxy, carboxy, alkylcarboxy, hydroxy, and alkoxyhydroxy.

34. A moisturizing formulation comprising:
(a) at least one dialkyl quat and at least one monoalkyl quat, wherein either
said at least one monoalkyl quat is a mixture of monoalkyl imidazoline quats, or
said at least one dialkyl quat is a mixture of dialkyl imidazoline quats;
(b) a solvent; and
(c) at least one ingredient chosen from a surfactant, fatty amine, amidoamine, sunscreen compounds, emollient, emulsifier, thickeners, absorbent, anti-acne agent, antiperspirant, anti-caking agent, antifoaming agent, antimicrobial agent, antioxidant, antiseptic agent, astringent, binder, buffer, biological additive, botanical extracts, buffering agent, bulking agent, chelating agent, chemical additive, coupling agent, conditioner, colorant, cosmetic astringent, cosmetic biocide, denaturant, drug astringent, detergent, dispersant, external analgesic, film former, foaming agent, fragrance component, humectant, hydrophobic ingredient, keratolytic, moisturizer, opacifying agent, pH adjuster, preservative, propellant, protein, retinoid, reducing agent, sequestrant, skin bleaching agent, softener, solubilizing agent, lubricant, penetrant, plastisizer, solvent and co-solvent, sunscreen additive, salt, silicone, essential oil, vitamin, wax, or mixtures thereof, said formulation being a moisturizer.

35. The moisturizing formulation of claim 34, wherein said solvent is selected from a group consisting of fatty alcohol, isopropyl alcohol, SDA-40, glycol and mixtures thereof.

36. The moisturizing formulation of claim 34, further comprising at least one amidoamine.

37. The moisturizing formulation of claim 34, wherein said dialkyl imidazoline quat is derived from HEAR oil and said monoalkyl quat is cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearamidopropyl PG-dimonium chloride phosphate, stearamidopropyl ethyldimonium ethosulfate, stearamidopropyl dimethyl(myristyl acetate)ammonium chloride, stearamidopropyl dimethyl cetearyl ammonium tosylate, stearamidopropyl dimethyl ammonium chloride, stearamidopropyl and dimethyl ammonium lactate.

38. The moisturizing formulation of claim 37, wherein said HEAR oil is a hydrogenated HEAR oil.

39. The moisturizing formulation of claim 34, wherein said mixture of dialkyl imidazoline quats includes at least one dialkyl imidazoline quat having at least one alkyl group having from 16 to 30 carbon atoms.

40. The moisturizing formula of claim 34, wherein said at least one monoalkyl quat includes at least one alkyl group having from 16 to 30 carbon atoms.

41. The moisturizing formulation of claim 24, wherein said at least one dialkyl quat is a dialkyl imidazoline quat of the formula (I):

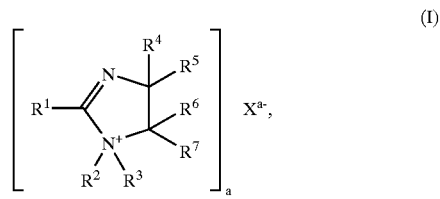

where X is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

a is the ionic charge of X;

$R^1$, $R^2$, and $R^3$ are independently hydrogen, $C_1$–$C_{30}$ alkyl, $C_1$–$C_{30}$ alkylhydroxy, $C_1$–$C_{30}$ alkyl amido $R_{(C1-C6)}$, $C_1$–$C_{30}$ alkylaryl amido $R_{(C1-C6)}$ or $C_1$–$C_{30}$ alkylhydroxy amido $R_{(C1-C6)}$, $R_{(C1-C6)}$ being $C_1$–$C_6$ alkylene or benzyl;

two of $R^1$, $R^2$, and $R^3$ are independently $C_{10}$–$C_{30}$ alkyl, $C_{10}$–$C_{30}$ alkylhydroxy, $C_{10}$–$C_{30}$ alkyl amido $R_{(C1-C6)}$, $C_{10}$–$C_{30}$ alkylaryl amido $R_{(C1-C6)}$ or $C_{10}$–$C_{30}$ alkylhydroxy amido $R_{(C1-C6)}$;

the remaining one of $R^1$, $R^2$ and $R^3$ is hydrogen, $C_1$–$C_8$ alkyl, $C_1$–$C_8$ alkylhydroxy, $C_1$–$C_8$ alkyl amido $R_{(C1-C6)}$, $C_1$–$C_8$ alkylaryl amido $R_{(C1-C6)}$ or $C_1$–$C_8$ alkylhydroxy amido $R_{(C1-C6)}$;

$R^4$, $R^5$, $R^6$ and $R^7$, same or different, are independently hydrogen, alkyl, arylalkyl, alkylaryl, fluoro, bromo, chloro, iodo, acetoxy, alkylacetoxy, arylacetoxy, carboxy, alkylcarboxy, hydroxy or alkoxyhydroxy.

42. The moisturizing formulation of claim 34, wherein said at least one dialkyl quat is a dialkyl imidazoline quat of the formula (II):

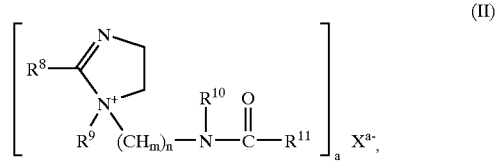

wherein X is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

a is the ionic charge of X;

n varies from 1 to 3;

m is 1 or 2;

$R^8$ and $R^{11}$, same or different, are independently $C_{16}$–$C_{30}$ alkyl or $C_{16}$–$C_{30}$ alkylhydroxy;

$R^9$ is hydrogen or $C_1$–$C_3$ alkyl; and $R^{10}$ is hydrogen, alkyl, arylalkyl, alkylaryl, fluoro, bromo, chloro, iodo, acetoxy, alkylacetoxy, arylacetoxy, carboxy, alkylcarboxy, hydroxy or alkoxyhydroxy.

43. The moisturizing formulation of claim 34, wherein said at least one said monoalkyl quat has the structure

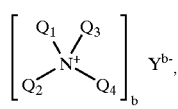

wherein Y is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

b is the ionic charge of Y;

$Q_1$ is selected from the group consisting of $C_{12}$–$C_{22}$ alkyl, $C_{12}$–$C_{22}$ alkyl amido $C_1$–$C_6$ alkylene, and $C_{12}$–$C_{22}$ alkylhydroxy; and $Q_2$, $Q_3$ and $Q_4$ are independently $C_1$–$C_6$ alkyl or benzyl.

44. The moisturizing formulation of claim 34, wherein said at least one monoalkyl quat os a monoalkyl quat of the formula (IV):

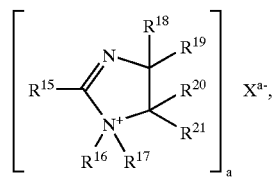

(IV)

wherein X is a salt-forming anion selected from the group consisting of chloride, bromide, iodide, fluoride, sulfate, methyl sulfate, methanebenzylsulfonate, phosphate, nitrite, nitrate, carboxylate, and mixtures thereof;

a is the ionic charge of X;

$R^{15}$, $R^{16}$ and $R^{17}$ are independently hydrogen, $C_1$–$C_{30}$ alkyl, $C_1$–$C_{30}$ alkylhydroxy, $C_1$–$C_{30}$ alkyl amido $R_{(C1-C6)}$, $C_1$–$C_{30}$ alkylaryl amido $R_{(C1-C6)}$, or $C_1$–$C_{30}$ alkylhydroxy amido $R_{(C1-C6)}$, wherein $R_{(C1-C6)}$ is a $C_1$–$C_6$ alkylene or benzyl;

one of $R^{15}$, $R^{16}$ and $R^{17}$ is $C_1$–$C_{30}$ alkyl, $C_{10}$–$C_{30}$ alkylhydroxy, $C_{10}$–$C_{30}$ alkyl amido $R_{(C1-C6)}$, $C_{10}$–$C_{30}$ alkylaryl amido $R_{(C1-C6)}$ or $C_{10}$–$C_{30}$ alkylhydroxy amido $R_{(C1-C6)}$;

the remaining two of $R^{15}$, $R^{16}$ and $R^{17}$ are independently hydrogen, $C_1$–$C_8$ alkyl, $C_1$–$C_8$ alkylhydroxy, $C_1$–$C_8$ alkyl amido $R_{(C1-C6)}$, $C_1$–$C_8$ alkylaryl amido $R_{(C1-C6)}$, or $C_1$–$C_8$ alkylhydroxy amido $R_{(C1-C6)}$;

$R^{18}$, $R^{19}$, $R^{20}$, and $R^{21}$, same or different, are independently selected from the group consisting of hydrogen, alkyl, arylalkyl, alkylaryl, fluoro, iodo, bromo and chloro, acetoxy, alkylacetoxy, arylacetoxy, carboxy, alkylcarboxy, hydroxy, and alkoxyhydroxy.

* * * * *

UNITED STATES PATENT AND TRADEMARK OFFICE
CERTIFICATE OF CORRECTION

PATENT NO. : 6,838,419 B2
DATED : January 4, 2005
INVENTOR(S) : Abel G. Pereira and Helena S. Barinova It is certified that error appears in the above-identified patent and that said Letters Patent is hereby corrected as shown below:

Column 1,
Line 19, "Compounds various personal" should read -- compounds, various personal --

Column 6,
Line 41, "group of the quat" should read -- groups of the quat --

Column 8,
Line 19, "mole" should be -- moles --

Column 24,
Line 12, "quat" should be -- quats --

Column 25,
Line 29, "improves" should be -- improve --

Column 28,
Line 37, "are" should be -- is --

Column 29,
Line 21, "or emollient" should read -- or more emollient --

Column 33,
Line 48, "(Mixture" should be -- (mixture) --
Line 49, "Quats of Hydrogenated Rapeseed Oil" should read "quats of hydrogenated rapeseed oil --

Column 41,
Line 66, "imidazoline quats of" should read -- imidazoline quat of --

UNITED STATES PATENT AND TRADEMARK OFFICE
CERTIFICATE OF CORRECTION

PATENT NO. : 6,838,419 B2
DATED : January 4, 2005
INVENTOR(S) : Abel G. Pereira and Helena S. Barinova It is certified that error appears in the above-identified patent and that said Letters Patent is hereby corrected as shown below:

Column 51,
Line 33, "quat os a" should read -- quat is a --

Signed and Sealed this

Tenth Day of May, 2005

JON W. DUDAS
*Director of the United States Patent and Trademark Office*